(12) United States Patent
Ram

(10) Patent No.: US 10,945,643 B2
(45) Date of Patent: Mar. 16, 2021

(54) MICROELECTRONIC SENSOR FOR BIOMETRIC AUTHENTICATION

(71) Applicant: EPITRONIC HOLDINGS PTE. LTD., Singapore (SG)

(72) Inventor: Ayal Ram, Singapore (SG)

(73) Assignee: EPITRONIC HOLDINGS PTE. LTD., Singapore (SG)

( * ) Notice: Subject to any disclaimer, the term of this patent is extended or adjusted under 35 U.S.C. 154(b) by 1018 days.

(21) Appl. No.: 15/478,061

(22) Filed: Apr. 3, 2017

(65) Prior Publication Data

US 2017/0258376 A1    Sep. 14, 2017

Related U.S. Application Data

(63) Continuation-in-part of application No. 15/157,285, filed on May 17, 2016, now abandoned, and a (Continued)

(51) Int. Cl.
*H01L 29/778* (2006.01)
*A61B 5/04* (2006.01)
(Continued)

(52) U.S. Cl.
CPC .......... *A61B 5/1172* (2013.01); *A61B 5/0022* (2013.01); *A61B 5/02* (2013.01);
(Continued)

(58) Field of Classification Search
CPC ............... H01L 29/778; H01L 29/7781; H01L 29/7782; H01L 29/84; H01L 29/86
(Continued)

(56) References Cited

U.S. PATENT DOCUMENTS 9,462,994 B2 * 10/2016 Rogers .................... A61B 7/04
2007/0114568 A1 * 5/2007 Simin ................. H01L 29/7787
257/192

(Continued)

OTHER PUBLICATIONS

S. Nakayama, K. Sawamura, K. Mohri, T. Uchiyama; "Pulse-Driven Magnetoimpedance Sensor Detection of Cardiac Magnetic Activity", Plos One, vol. 6, Issue 10, e25834. (2011).
(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

In some embodiments, a microelectronic sensor includes an open-gate pseudo-conductive high-electron mobility transistor and used for biometric authentication of a user. The transistor comprises a substrate, on which a multilayer hetero-junction structure is deposited. This hetero-junction structure comprises a buffer layer and a barrier layer, both grown from III-V single-crystalline or polycrystalline semiconductor materials. A two-dimensional electron gas (2DEG) conducting channel is formed at the interface between the buffer and barrier layers and provides electron current in the system between source and drain electrodes. The source and drain contacts, which maybe either ohmic or non-ohmic (capacitively-coupled), are connected to the formed 2DEG channel and to electrical metallizations, the latter are placed on top of the transistor and connect it to the sensor system. The metal gate electrode is placed between the source and drain areas on or above the barrier layer, which may be recessed or grown to a specific thickness. An optional dielectric layer is deposited on top of the barrier layer.

24 Claims, 27 Drawing Sheets

Related U.S. Application Data continuation-in-part of application No. 15/067,093, filed on Mar. 10, 2016, now abandoned.

(60) Provisional application No. 62/362,165, filed on Jul. 14, 2016.

(51) Int. Cl.

| | | |
|---|---|---|
| A61B 5/1172 | (2016.01) | |
| H01L 23/538 | (2006.01) | |
| H01L 23/66 | (2006.01) | |
| H01L 29/51 | (2006.01) | |
| A61B 5/18 | (2006.01) | |
| A61B 5/00 | (2006.01) | |
| A61B 5/02 | (2006.01) | |
| A61B 5/0507 | (2021.01) | |
| A61B 5/117 | (2016.01) | |
| H04W 4/80 | (2018.01) | |
| H01L 29/08 | (2006.01) | |
| H01L 29/417 | (2006.01) | |
| H01L 29/06 | (2006.01) | |
| H01L 29/20 | (2006.01) | |

(52) U.S. Cl.
CPC .............. *A61B 5/04* (2013.01); *A61B 5/0507* (2013.01); *A61B 5/117* (2013.01); *A61B 5/18* (2013.01); *A61B 5/681* (2013.01); *A61B 5/6893* (2013.01); *A61B 5/6897* (2013.01); *A61B 5/6898* (2013.01); *H01L 23/5387* (2013.01); *H01L 23/66* (2013.01); *H01L 29/513* (2013.01); *H01L 29/7783* (2013.01); *A61B 2562/028* (2013.01); *A61B 2562/166* (2013.01); *H01L 29/0657* (2013.01); *H01L 29/0843* (2013.01); *H01L 29/2003* (2013.01); *H01L 29/41766* (2013.01); *H01L 29/51* (2013.01); *H01L 29/7781* (2013.01); *H01L 29/7787* (2013.01); *H04W 4/80* (2018.02)

(58) Field of Classification Search
USPC ................................................ 257/194–195
See application file for complete search history.

(56) References Cited

U.S. PATENT DOCUMENTS

| | | | | | |
|---|---|---|---|---|---|
| 2008/0265258 | A1* | 10/2008 | Tanabe | ................ | H01L 29/7787 257/76 |
| 2009/0072272 | A1* | 3/2009 | Suh | ..................... | H01L 29/7783 257/194 |
| 2010/0320505 | A1* | 12/2010 | Okamoto | .......... | H01L 29/41766 257/192 |
| 2011/0199102 | A1* | 8/2011 | Garcia | ............... | G01N 27/4148 324/658 |
| 2011/0220965 | A1* | 9/2011 | Ohki | ................. | H01L 29/66462 257/194 |
| 2014/0203797 | A1* | 7/2014 | Stivoric | ................. | G01K 1/022 324/76.11 |
| 2014/0323895 | A1* | 10/2014 | Vitushinsky | ........ | H01L 29/7786 600/523 |
| 2019/0194796 | A1* | 6/2019 | Fujioka | ................... | C23C 14/34 |

OTHER PUBLICATIONS

J. An, H. Li, L. Miao, S. Qin; "A Study on Human Magnetocardiogram Using Giant Magneto-impedance Sensor", Second International Conference on Electronics, Communications and Control. (2012).

Y. Kado, M. Shinagawa ; "RedTacton Near-body Electric-field Communications Technology and Its Applications", NTT Technical Review, vol. 8, No. 3. (2010).

S. D. Burnham, K. Boutros, P. Hashimoto, C. Butler, D. W. S. Wong, M. Hu, and M. Micovic,; "Gate-recessed normally-off GaN-on-Si HEMT using a new O2-BCl3 digital etching technique", Phys. Status Solidi C, vol. 7, No. 7-8, pp. 2010-2012. (2010).

C. Y. Chang, S. J. Pearton, C. F. Lo, F. Ren, I. I. Kravchenko, A. M. Dabiran, A. M. Wowchak, B. Cui, and P. P. Chow; "Development of enhancement mode AlN/GaN high electron mobility transistors", Appl. Phys. Lett., vol. 94, No. 26, p. 263505. (2009).

R. Vitushinsky, M. Crego-Calama, S. H. Brongersma, and P. Offermans; "Enhanced detection of NO2 with recessed AlGaN/GaN open gate structures", Applied Physics Letters 102, 172101. (2013).

H. Chen, M. Wang, and K. J. Chen,"Enhancement-mode AlGaN/GaN HEMTs Fabricated by Standard Fluorine Ion Implantation", in CS MANTECH Conference, May 17-20, 2010, Portland, Oregon, USA, pp. 145-148. (2010).

Ma Xiao-Hua, Pan Cai-Yuan, Yang Li-Yuan, Yu Hui-You, Yang Ling, Quan Si, Wang Hao, Zhang Jin-Cheng, and Hao Yue, "Characterization of Al2O3/GaN/AlGaN/GaN metal insulator semiconductor high electron mobility transistors with different gate recess depths", in Chin. Phys. B vol. 20, No. 2, 027304. (2011).

Raphael Brown, Douglas Macfarlane, Abdullah Al-Khalidi, Xu Li, Gary Ternent, Haiping Zhou, Iain Thayne, and Edward Wasige, "A Sub-Critical Barrier Thickness Normally-Off AlGaN/GaN MOS-HEMT", IEEE Electron Device Letters, vol. 35, No. 9, pp. 906-908. (2014).

\* cited by examiner

Fig. 5a             Ga-Face Polarity
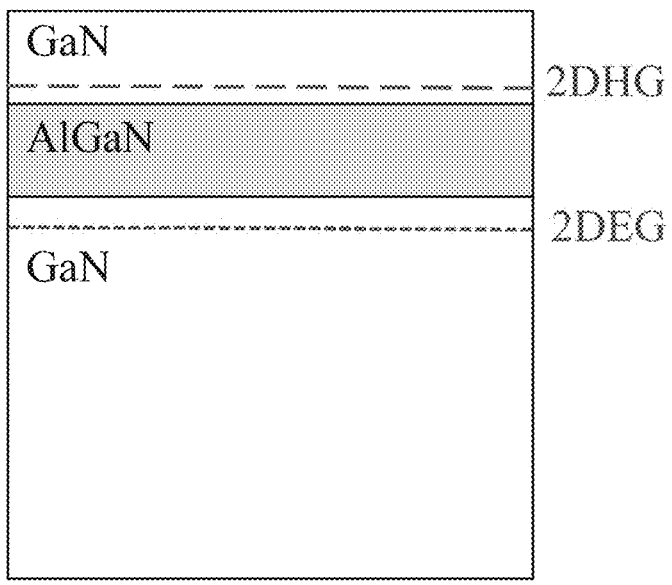
Fig. 5b             N-Face Polarity
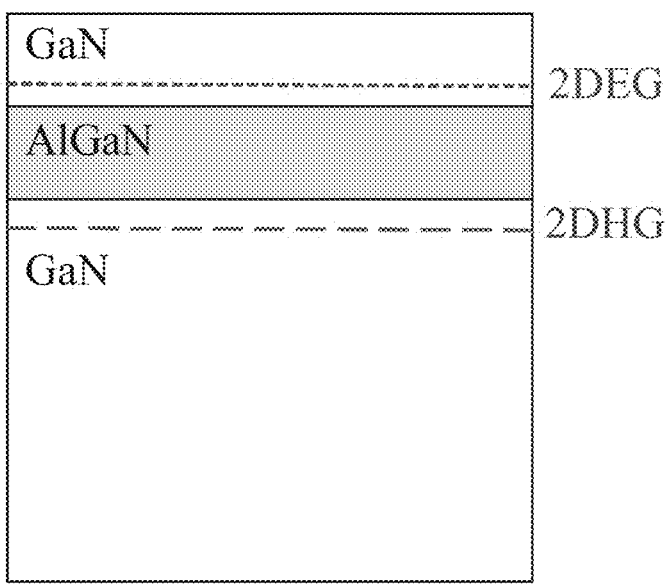

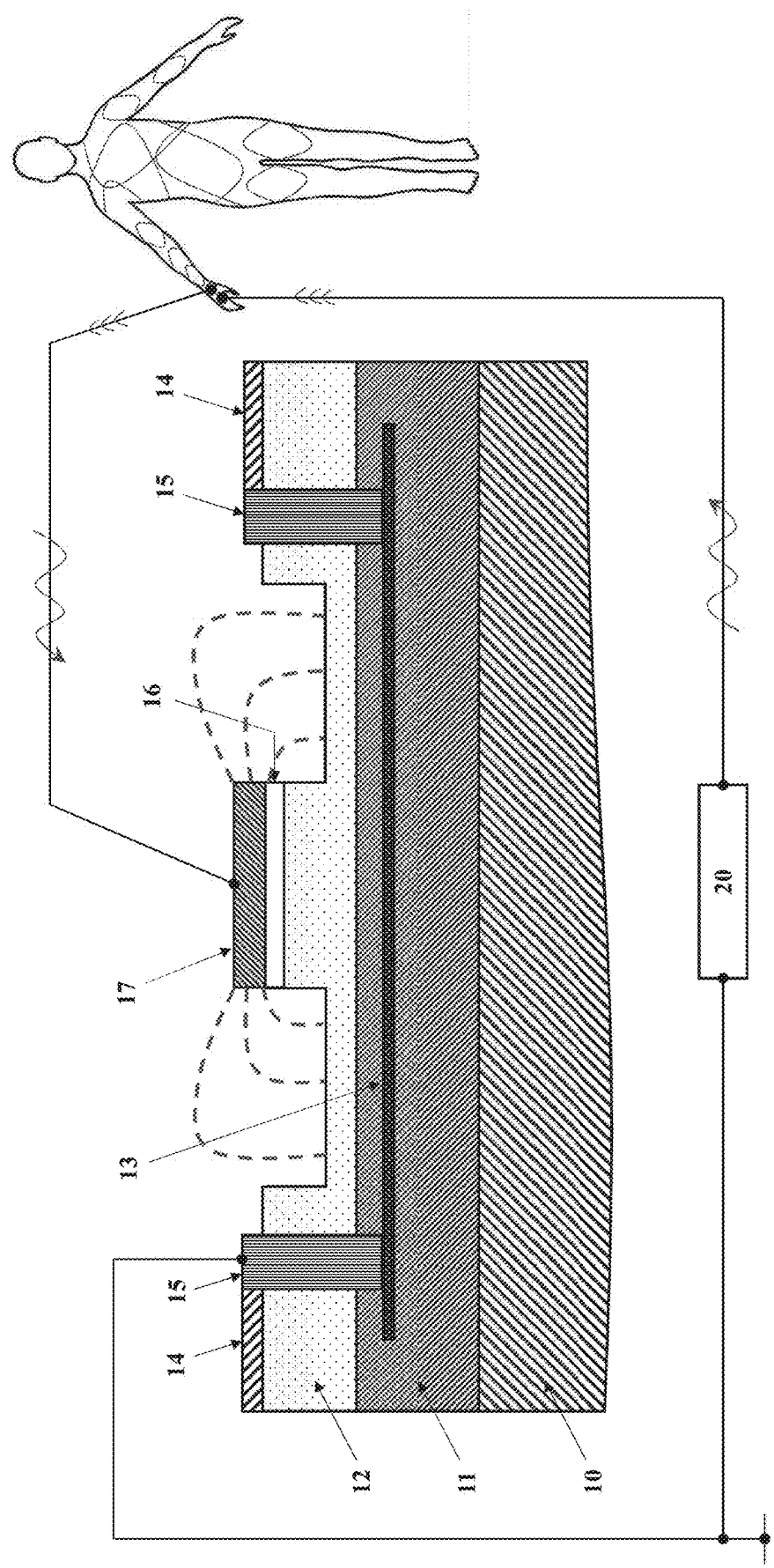

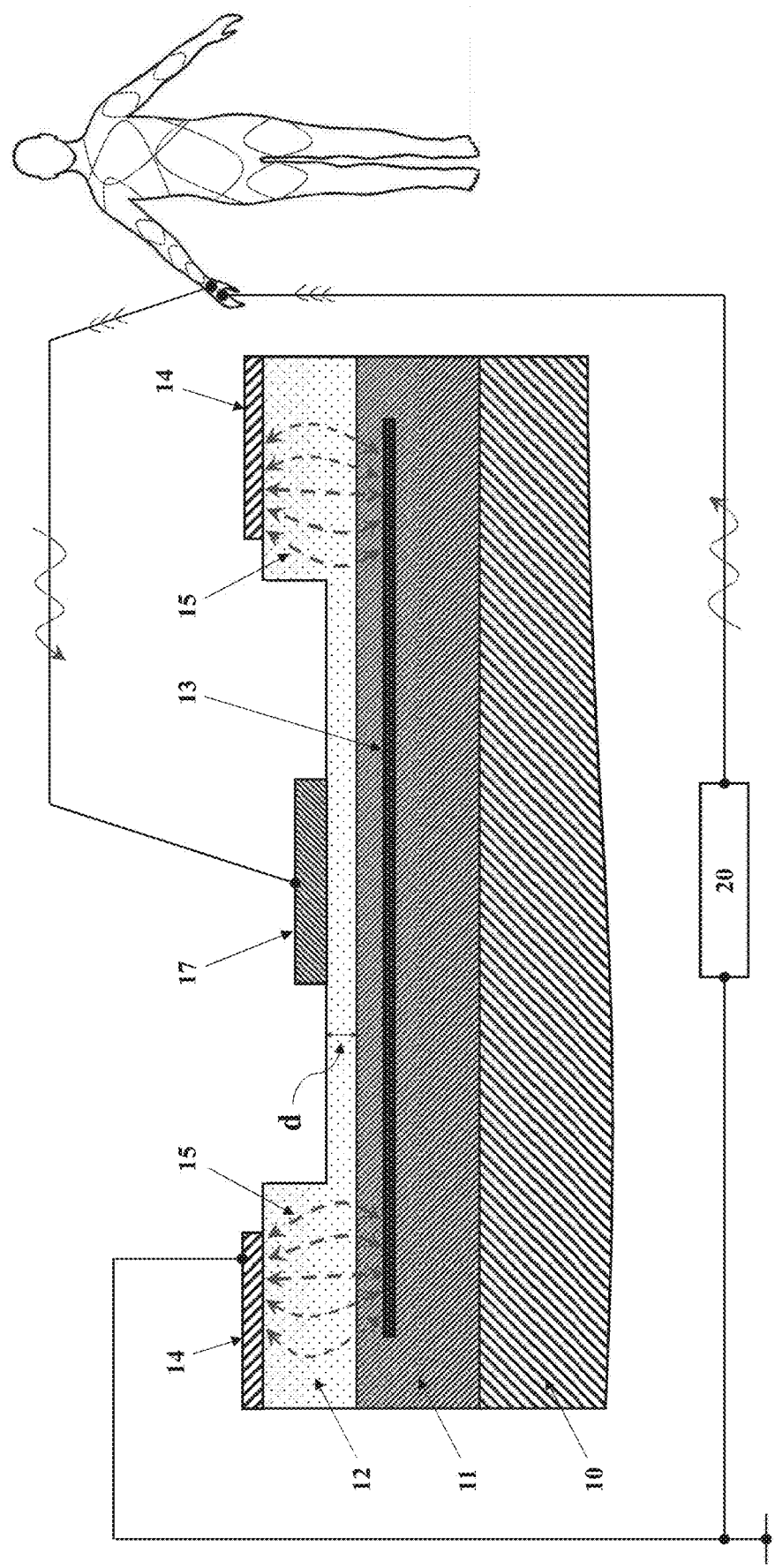

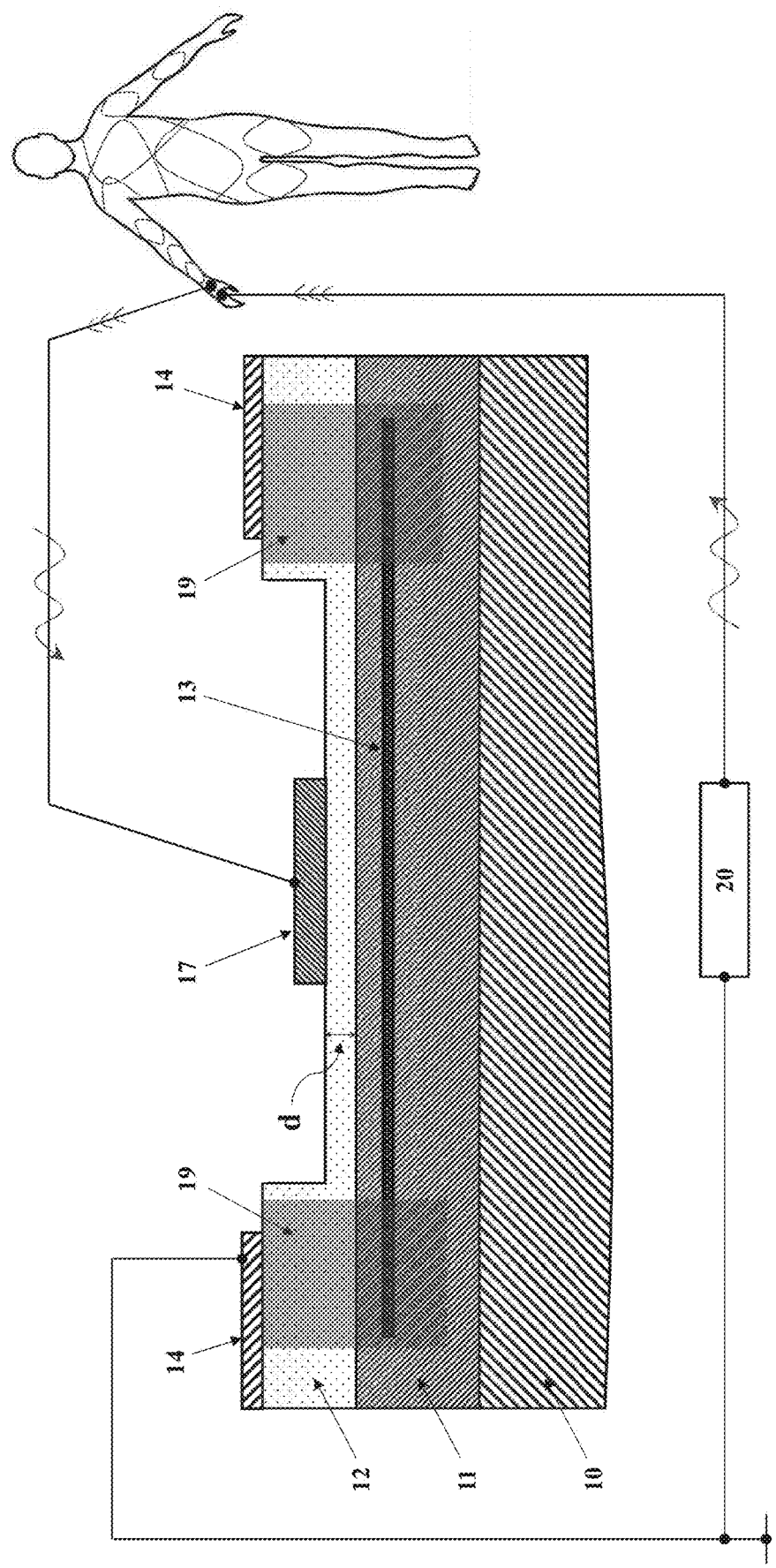

User 1

User 2

User 3

User 4

User 5

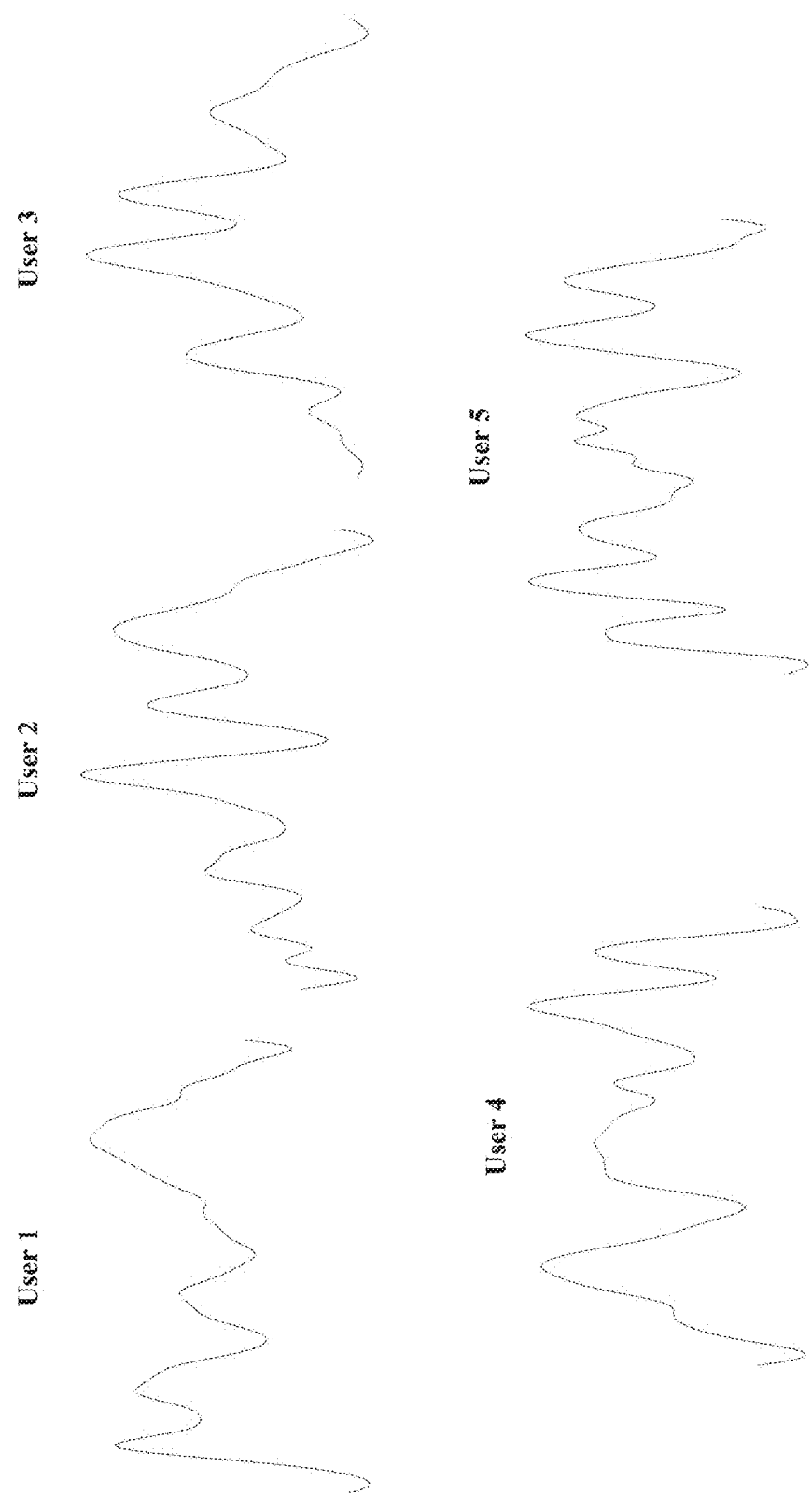

MICROELECTRONIC SENSOR FOR BIOMETRIC AUTHENTICATION

TECHNICAL FIELD

The present application relates to the field of microelectronic sensors based on high-electron-mobility transistors and their use in detection and continuous monitoring of electrical signals generated by a human body. In particular, the present application relates to the open-gate pseudo-conductive high-electron-mobility transistors and their use in a biometric authentication.

BACKGROUND

There are many different types of biometric authentication systems nowadays used in smartphones, key locks, airport and high security locations where an extremely high level of authentication is required. Commercially available authentication systems may include a fingerprint ID sensor, an iris ID sensor or speech recognition. However, these systems proved to have a relatively low security level.

In 2014, a new type of the biometric authentication device by Bionym, based on the electrocardiogram (ECG), has been introduced on the market. This device, called "Nymi", is capable of capturing a unique electrocardiographic waveform of a person, and further maps it to ECG patterns. Nymi is continuously worn as a bracelet or wristband on the user's wrist and uses learning algorithms to memorise the user's ECG patterns in order to increase the quality and authentication level of the user. WO 2012151680 by Bionym discloses a biometric sensor based on the analysis of the ECG signals used to authenticate one or more individuals. This sensor relies on authenticating identity by matching the overall shape of the user's ECG waveform (captured via an electrocardiogram sensor). Unlike other authentication methods, such as fingerprint scanning and iris-recognition, the sensor by Bionym sustains authentication so long as the wearer keeps the wristband on. To authenticate via Nymi, the user puts the wristband on and touches a topside sensor with one hand to complete an electrical loop with the bottom-side sensor touching their wrist. That generates the ECG data used to authenticate their identity, and the wristband transmits the ECG via Bluetooth to the corresponding registered app, on a smartphone or other external device in proximity to the user, to verify the wearer's identity.

The biometric authentication devices, such as Nymi, and similar ECG-based devices however have several drawbacks. First, they use a single data source (ECG) for mapping the users' unique ID profiles, making them a prime target for signal cloning and similar security-breaking techniques. Second, these devices are not closed systems and cannot provide a single closed integrated chip solution, which can be considered another tampering and security-breaching issue on a hardware level. Nymi needs to be worn at all times, in order to use the authentication system, which may be intrusive to some users. In addition, Nymi and similar ECG-based devices do not provide a single-contact point for simple authenticate of a user, and require the user to perform rather complex steps and procedures to authenticate themselves prior to each use, for example to use both hands to close a circuit and authenticate the user, the process each user must perform on a daily basis. Therefore, these technologies cannot be integrated directly into end-point devices, such as credit cards and mobile phones, for a single-point authentication.

However, there are two major disadvantages of using the above ECG-based sensors. First, many medications and various psychological conditions can directly affect, change and alter the heart rhythmic cycles, which are recorded by the sensor, so that the general authentication system may fail at times. Second, the ECG-based sensor or similar sensor sensing the hemodynamic electrical signals of the heart and lungs requires a full heart cycle or even two in order to authenticate the user. In a real-world application, this is a huge drawback in comparison to the existing capacitive fingerprint sensors, since it would take too long to authenticate the user or, for example to unlock a phone, compared to existing one-second authentication time.

In view of the above, there is a long-felt need to develop a new biometric authentication sensor based on recording the user's physiological signals, which would overcome the aforementioned drawbacks of the existing ECG-based sensors measuring the heart dipole cycle.

SUMMARY

The present application describes embodiments of a method for monitoring physiological parameters of a human subject using a microelectronic sensor based on an open-gate pseudo-conductive high-electron mobility transistor (PC-HEMT). In some embodiments, a transistor comprises a substrate, on which a multilayer hetero-junction structure is deposited. This hetero-junction structure may comprise at least two layers, a buffer layer and a barrier layer, which are grown from III-V single-crystalline or polycrystalline semiconductor materials.

A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between source and drain electrodes. The source and drain, either ohmic or capacitively-coupled (non-ohmic) contacts are connected to the formed 2DEG/2DHG channel and to electrical metallizations, the latter are placed on top of the transistor and connect it to the sensor system. An optional dielectric layer is deposited on top of the hetero-junction structure. The open gate area of the transistor is formed between the source and drain areas as a result of recessing or growing of the top layer to a specific thickness.

If the source and drain contacts are non-ohmic (capacitively-coupled), in order to electrically contact the 2DEG/2DHG channel underneath, which is about 5-20 nm bellow metallizations, the AC-frequency regime is used. The capacitive coupling of the non-ohmic metal contacts with the 2DEG/2DHG channel is normally induced at the frequency higher than 30 kHz. In the case of non-ohmic contacts, the DC readout cannot be carried out. Instead, the AC readout or impedance measurements of the electric current flowing through the 2DEG/2DHG-channel are performed.

In some embodiments, the significant features of the PC-HEMT structure are that:

(i) the thickness of the top layer in the open gate area between the source and drain contacts is 5-9 nm, preferably 6-7 nm, more preferably 6.3 nm, and that corresponds to the pseudo-conducting current range between normally-on and normally-off operation mode of the transistor, (ii) the surface of the top layer within the open gate area between the source and drain contacts has a roughness of about 0.2 nm or less, preferably 0.1 nm or less, more preferably 0.05 nm, and (iii) the non-ohmic source and drain contacts for the capacitive coupling with the conductive 2DEG/2DHG channel optionally replace the ohmic contacts.

In some embodiments, the PC-HEMT multilayer hetero-junction structure of the present application is grown from any available III-V single-crystalline or polycrystalline semiconductor materials, such as GaN/AlGaN, GaN/AlN, GaN/InN, GaN/InAlGaN, GaAs/AlGaAs GaN/InAlN, InN/InAlN, and $LaAlO_3/SrTiO_3$.

In case of the GaN/AlGaN PC-HEMT, it has been surprisingly found that in the open gate area of the PC-HEMT, the thickness of the top layer that corresponds to the pseudo-conducting current range between normally-on and normally-off operation mode of the PC-HEMT, is about 6-7 nm.

In a particular embodiment, the hetero-junction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the transistor.

In some embodiments, the present application provides the PC-HEMT-based microelectronic senor for biometric authentication and method for using thereof.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

Disclosed embodiments will be understood and appreciated more fully from the following detailed description taken in conjunction with the appended figures.

FIG. 5a schematically shows the formation of the 2DEG and 2DHG conducting channels in the Ga-face three-layer AlGaN/GaN PC-HEMT structure.

FIG. 5b schematically shows the formation of the 2DEG and 2DHG conducting channels in the N-face three-layer AlGaN/GaN PC-HEMT structure.

FIG. 6a shows a cross-sectional view of the PC-HEMT of an embodiment with a non-recessed AlGaN barrier layer and with an RF generator.

FIG. 7a schematically shows a cross-sectional view of the PC-HEMT of an embodiment with capacitively-coupled non-ohmic source and drain contacts, without a dielectric layer and with an RF generator.

FIG. 7b schematically shows a cross-sectional view of the PC-HEMT of an embodiment with highly-doped source and drain areas and with an RF generator.

FIGS. 11m-11n shows the cardio-pulmonary hemodynamic data recorded with the sensor of an embodiment for User 5 with the 20 Hz low-pass filter and 1-20 Hz band-pass filter.

FIG. 12a shows the single heart cycles extracted from the above data for the five users.

DETAILED DESCRIPTION

Figure 1A:
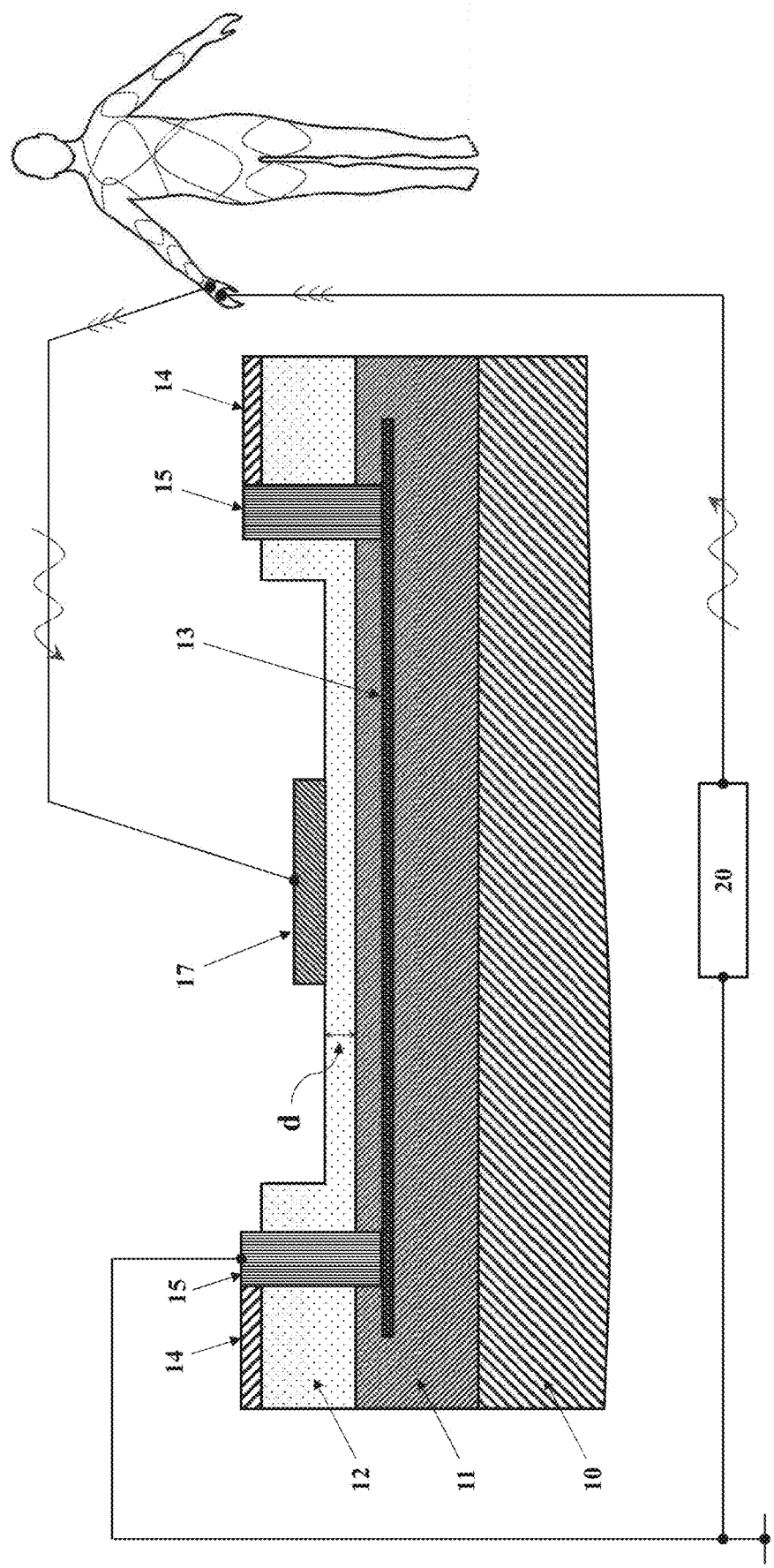
FIG. 1a schematically shows a cross-sectional view of the PC-HEMT of an embodiment without a dielectric layer and with an RF generator.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. As used herein, the term "about" means there is a 10% tolerance of the mentioned or claimed value. As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Unlike the ECG-based biometric devices, such as Nymi, which is mentioned in the background section, the sensor of embodiments uses relatively complex waveforms recorded from the user's heart rhythmic cycles, hemodynamics of the right atrium and left atrium, pulmonary cycles, intestine, electromyography (EMG) of the nervous system, circulatory system and biomechanical waveforms generated by the user's internal organs. In addition, it is about $1 \times 10^9$ times mores sensitive than the Nymi device or any similar commercially available ECG-based sensor.

However, as mentioned above, the major problem with the Nymi-type devices or any ECG-based sensors is their pronounced sensitivity to physiological conditions of a user. Many medications and various psychological conditions can directly affect, change and alter the heart rhythmic cycles, which are recorded by the sensor, so that the general authentication system may fail at times. On top of that, the ECG-based sensor or similar sensor sensing the hemodynamic electrical signals of the heart and lungs requires a full heart cycle or even two in order to authenticate the user. In a real-world application, this is a huge drawback in comparison to the existing capacitive fingerprint sensors, since it would take too long to authenticate the user or, for example to unlock a phone, compared to existing single-second authentication time.

The sensor of an embodiment of the present application is able to record a total one-time mapping of electrical fields produced by the user's internal body organs, for a digital snapshot of the user, which is completely unique as the user's genetic code. The biometric authentication sensor of embodiments integrated into a monolithic printed-circuit board (PCB) chip performs the authentication completely on the hardware layer. It is essentially a closed end-to-end system requiring only a single point of contact to the user's body point at the time of authentication and having the highest level of security. Unlike any other biometric authentication devices, the biometric authentication sensor of embodiments is capable of detecting with its proximity sensor a user's distance and to prepare for instant and real-time authentication. In addition, the instant biometric sensor does not need to be continuously worn on the user to learn the user's ECG data, but takes a one-time single snapshot during the setup to authenticate the user at any time.

Eventually, in contrast to Nymi or similar ECG-based biometric devices, the biometric sensor of embodiments can be integrated into any type of electronic system for a system switch, for the authentication of the user, or for locking devices on their hardware layer, where software does not play a role, and the highest level of security therefore can be achieved. For example, the biometric sensor of embodiments may be integrated into a mobile phone holder casing or as a sticker on the phone. In addition, the sensor can be used to block and lockout memory cells on sensitive data devices and credit cards as a built-in integrated circuit (on a PCB) or as a standalone device. The latter is connected via Bluetooth to lock any device, by fixing this device to any Bluetooth connected device. The biometric system can also be integrated directly as a component into a smartphone to provide a hardware layer lock to the phone or device, which creates a secure layer to the device's hardware with no authentication.

The biometric authentication sensor of embodiments is based on the open-gate pseudo-conductive high-electron mobility transistor (PC-HEMT) described, for example in the co-pending patent application U.S. Ser. No. 15/157,285, from which the present application claims priority. The phenomenon of the pseudo-conductive current described in that application makes the biometric sensor of embodiments of the present application extremely sensitive.

In brief, working principle of the PC-HEMT sensor is based on ultra-high charge sensitivity at the sensor/body tissue surface interface. For example, a human heart physically represents a volume source of an electric dipole field acting within a volume electrolytic conductor represented by human body. Using the enormously high charge sensitivity, it is possible to record both processes: an appearance and wave (dynamic distribution) of an electrical heart dipole due to a heart muscle polarisation/depolarisation cycles, followed by corresponding mechanical movements of polarised heart parts in a real time. The graphical user interface (GUI) of the sensor of embodiments of the present application is programmed in such a way as to interpret the complex signal peaks (waveforms) recorded with the sensor from user's heart rhythmic cycles, hemodynamics of the right atrium and left atrium, pulmonary cycles, intestine, electromyography of the nervous system, circulatory system and biomechanical waveforms generated by the user's internal organs, process their shape and time intervals, and correlate them, for example with the corresponding ECG peak/point readings of P, Q, R, S, T and J peaks, and with related intervals between said points in the electrocardiogram.

In one aspect of the present application, FIG. 1a shows a cross-sectional view of the PC-HEMT of an embodiment of the present application with a radio-frequency generator (20) connected to the PC-HEMT, said PC-HEMT comprising:

a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts (15);

the source and drain contacts (15) connected to said 2DEG or 2DHG conducting channel (13) and to electrical metallizations (14) for connecting said transistor to an electric circuit;

a metal gate electrode (17) placed directly on said barrier layer (12) between said source and drain contacts (15) and electrically connected to a wire contact with any single body point;

wherein:
(i) the thickness (d) of said barrier layer (12) beneath said metal gate electrode (17), between said source and drain contacts (15), is about 5-9 nm which corresponds to the pseudo-conducting current range between normally-on and normally-off operation mode of the transistor, and
(ii) the surface of said barrier layer (12) has a roughness of about 0.2 nm or less.

Figure 1B:
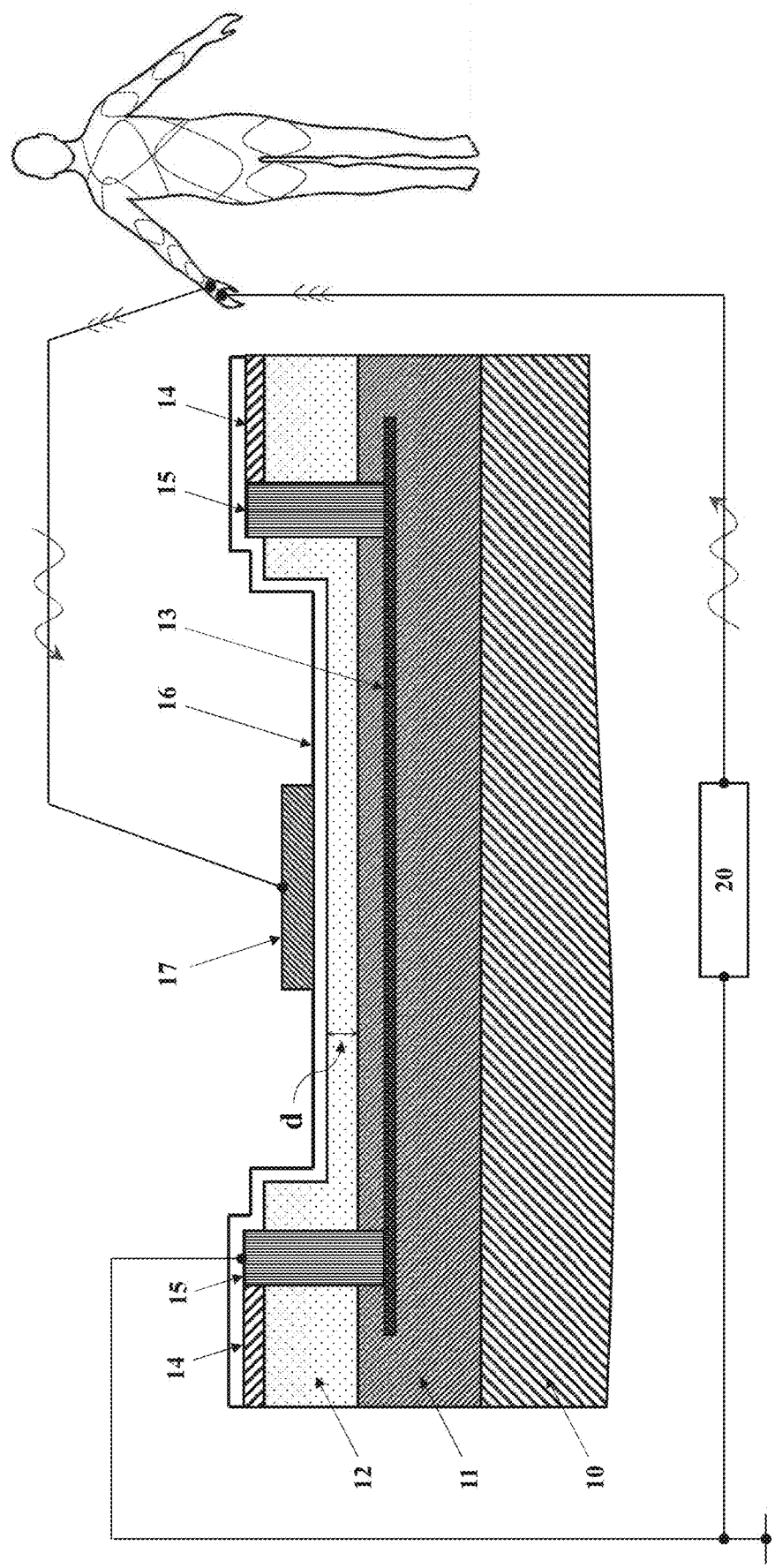
FIG. 1b schematically shows a cross-sectional view of the PC-HEMT of an embodiment with a dielectric layer and with an RF generator.

The PC-HEMT, which is shown on FIG. 1a, may further comprise a dielectric layer (16) of 1-10 nm thickness. This dielectric layer (16) is deposited on top of the barrier layer (12), as schematically shown in FIG. 1b. Metal gate electrode (17) is then placed directly on the dielectric layer (16) and is electrically connected to a wire contact with any single body point. This configuration prevents strong electrical leakage at the metal/barrier layer interface.

In a further embodiment, the dielectric layer (16) used for device passivation, is made, for example, of SiO—SiN—SiO ("ONO") stack of 100-100-100 nm thickness or SiN—SiO—SiN ("NON") stack having the same thicknesses. This dielectric layer (16) is deposited on top of the barrier layer by a method of plasma-enhanced chemical vapour deposition (PECVD), which is a stress-free deposition technique.

In a specific embodiment, the III-V semiconductor materials are selected from the pairs of GaN/AlGaN, GaN/AlN, GaN/InN, GaN/InAlN, InN/InAlN, GaN/InAlGaN, GaAs/AlGaAs and $LaAlO_3/SrTiO_3$.

The electrical metallizations (14) connect the transistor to the electric circuit and allow the electric current to flow between ohmic contacts (15) via the two-dimensional electron gas (2DEG) channel (13). The metallizations (14) are made of metal stacks, such as Cr/Au, Ti/Au, Ti/W, Cr/Al and Ti/Al. The Cr or Ti layers of the metal stack is, for example, of 5-10 nm thickness, while the second metal layer, such as Au, W and Al, is of 100-400 nm thickness. The metallizations (14) are chosen according to the established technology and assembly line at a particular clean room fabrication facility. In yet further embodiment, the source and drain ohmic contacts (15) are made of metal stacks, such as Ti/Al/Mo/Au, Ti/Al/Ni/Au, Ti/Au and Ti/W having 15-50 nm thickness.

In some embodiments, substrate layer (10) comprises a suitable material for forming the barrier layer and is composed, for example, of sapphire, silicon, silicon carbide, gallium nitride or aluminium nitride. The hetero-junction structure (11,12) is deposited on the substrate layer (10), for example, by a method of metalorganic chemical vapour deposition (MOCVD), and forms the 2DEG or 2DHG channel (13) in the close proximity to the interface between the buffer layer (11) and the barrier layer (12). The barrier layer (12) then may be either recessed or grown as a thin layer between the source and drain contacts (15).

The 2DEG or 2DHG channel (13) formed near the interface between the buffer layer (11) and the barrier layer (12) serves as a main sensitive element of the transistor reacting to a surface charge and potential. The 2DEG or 2DHG channel (13) is configured to interact with very small variations in surface or proximal charge or changes of electrical field on the barrier layer/metal gate interface interacting with the donor-like surface trap states of the barrier layer. This will be discussed below in detail.

The term "2DEG" mentioned in the following description and claims should not be understood or interpreted as being restricted to the two-dimensional electron gas. As stated above and will be explained later in this application, the two-dimensional hole gas may also be a possible current carrier in a specific hetero-junction structure. Therefore, the term "2DEG" may be equally replaced with the term "2DHG" without reference to any specific PC-HEMT configuration.

Thus, the significant features of the PC-HEMT structure are:
(i) the barrier layer (12) has a thickness of 5-9 nm in the gate area (d) between the source and drain contacts (15), preferably 6-7 nm, more preferably 6.3 nm, which corresponds to the pseudo-conducting current range between normally-on and normally-off operation mode of the transistor, and
(ii) the surface of this barrier layer (12) within the gate area has a roughness of 0.2 nm or less, preferably 0.1 nm or less, more preferably 0.05 nm.

The above specific thickness of the barrier layer (12) beneath the metal gate electrode (17), between the source and drain contacts, is achieved by either dry etching the semiconductor material of this layer, i.e. recessing the barrier layer with the etching rate of 1 nm per 1-2 min in a controllable process, or coating the buffer layer (11) with an ultrathin layer of the III-V semiconductor material. In order to increase the charge sensitivity of the transistor, the surface of the recessed ultrathin barrier layer is post-treated with plasma (chloride) epi-etch process. Consequently, the natively passivated surface is activated by the plasma etch to create an uncompensated (ionised) surface energy bonds or states, which are neutralized after MOCVD growing.

Figure 2:
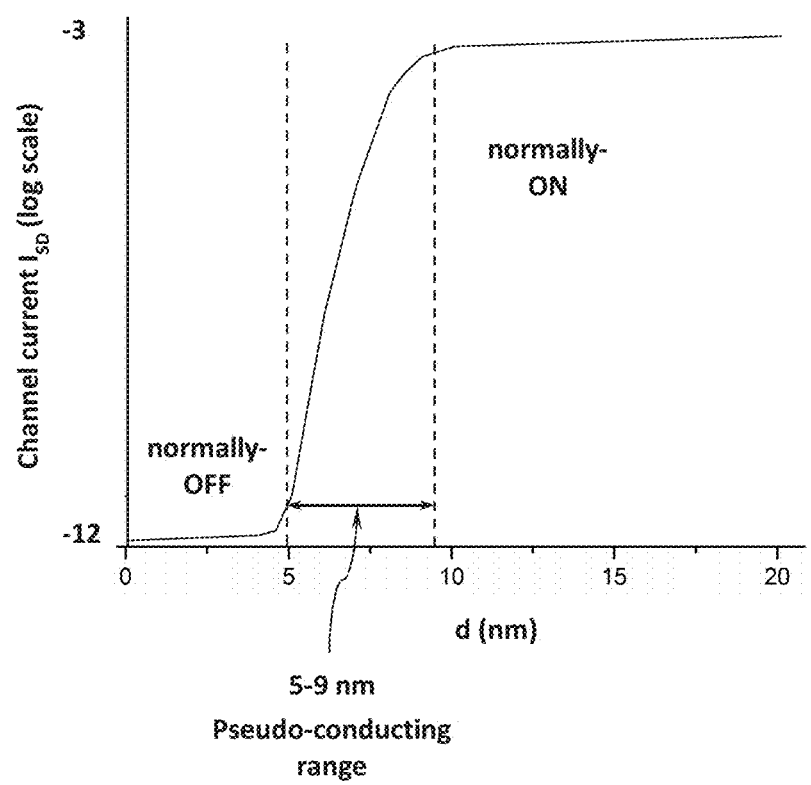
FIG. 2 schematically shows the dependence of the source-drain current (a charge carrier density) induced inside the 2DEG channel of a GaN/AlGaN HEMT on the thickness of the AlGaN barrier layer recessed in the open gate area.

FIG. 2 shows the dependence of the source-drain current (a charge carrier density) on the recessed barrier layer thickness. As seen from the plot, the HEMTs that have a thickness of the barrier layer larger than about 9 nm are normally-on devices. In such devices, due to the inherent polarisation effects present in the III-V materials, a thin sheet of charges is induced at the top and bottom of the interfaces of the barrier layer. As a result, a high electric field is induced in the barrier layer, and surface donor states at the top interface start donating electrons to form the 2DEG channel at the proximity of the hetero-junction interface without the application of a gate bias. These HEMTs are therefore normally-on devices. On the other hand, the HEMTs that have a thickness of the barrier layer in the open gate area lower than about 5 nm act as normally-off devices.

The barrier layer recessed or grown to 5-9 nm is optimised for significantly enhancing sensitivity of the PC-HEMT sensor. This specific thickness of the barrier layer corresponds to the "pseudo-conducting" current range between normally-on and normally-off operation modes of the transistor. "Pseudo-contacting" current range of the HEMT is defined as an operation range of the HEMT between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps at the surface of the barrier layer of the transistor are one of the most important sources of the 2DEG in the channel. However, this only applies for a specific barrier layer thickness. In a relatively thin barrier layer, the surface trap state is below the Fermi level. However, as the barrier layer thickness increases, the energy of the surface trap state approaches the Fermi energy until it coincides with it. The thickness of the barrier layer corresponding to such situation is defined as "critical". At this point, electrons filling the surface trap state are pulled to the channel by the extremely strong polarisation-induced electric field found in the barrier to form the 2DEG instantly.

If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, crystal defects are created at the interface between the buffer and the barrier layers, and the piezoelectric polarisation completely disappears causing deterioration in the 2DEG density.

Figure 3:
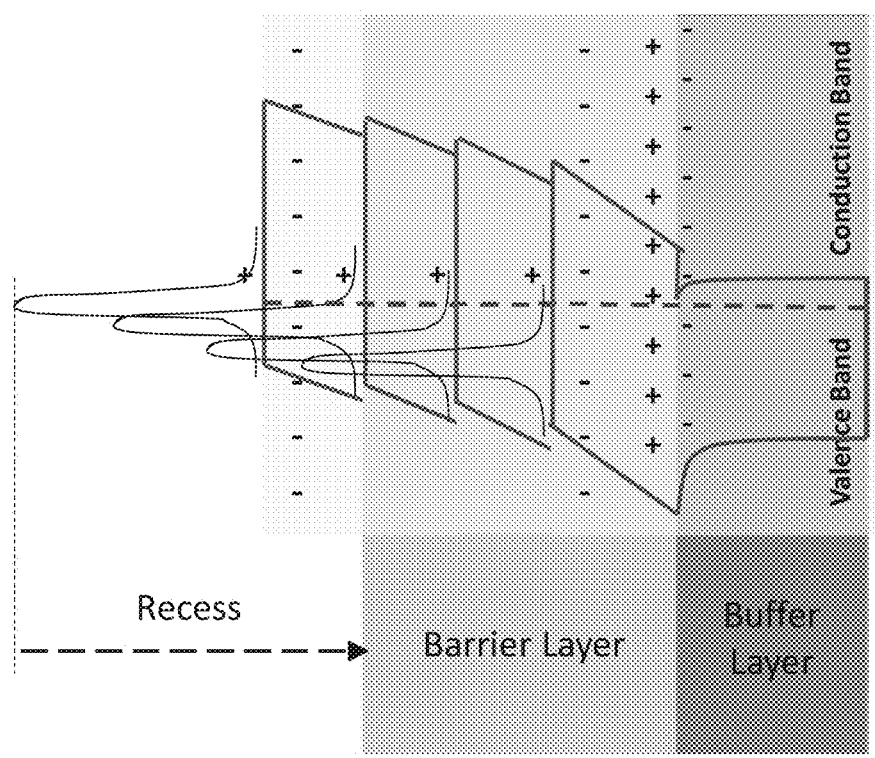
FIG. 3 illustrates a theory behind the 2DEG formation (charge neutrality combined with the lowest energy level) at the conduction band discontinuity.

In order to illustrate the above phenomenon of the pseudo-conducting current discovered by the authors of the present application, reference is now made to the following figures. As mentioned above, FIG. 2 shows the dependence of the source-drain current (a charge carrier density) on the recessed AlGaN barrier layer thickness. An energy equilibrium between the donor surface trap states and the AlGaN tunnel barrier leads to the 2DEG formation (charge neutrality combined with the lowest energy level) at the conduction band discontinuity. As explained above, decrease in the thickness of the barrier layer results in increase of the energy barrier. As a result, the ionisable donor-like surface trap states responsible for electron tunnelling from the surface to the 2DEG drift bellow the Fermi level, thereby minimizing the electron supply to the 2DEG channel. This theoretical situation is illustrated in FIG. 3. Therefore, the recess of the AlGaN layer from 9 nm to 5 nm leads to extremely huge drop in the 2DEG conductivity for six orders of magnitude.

Thus, the mechanism of the 2DEG depletion based on recessing the barrier layer is strongly dependent on the donor-like surface trap states (or total surface charge). As the thickness of the barrier layer decreases, less additional external charge is needed to apply to the barrier layer surface in order to deplete the 2DEG channel. There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, such as surface charging or reaction, leads immediately to the very strong 2DEG depletion. As a result, the surface of the barrier layer at this critical thickness is extremely sensitive to any smallest change in the electrical current of the metal gate.

Vitushinsky et al (2013) has recently proved the above concept of pseudo-conducting by demonstrating that recessing AlGaN barrier layer of AlGaN/GaN hetero-structures in the open gate area can dramatically enhance the sensitivity of the transistor to surface interactions. They investigated the response to ppb levels of $NO_2$ in humid conditions, which finds application in air quality monitoring. They demonstrated that when the AlGaN barrier layer is relatively thick (22 nm), the surface charge sensitivity is around six orders of magnitude smaller compared to 6.3 nm AlGaN barrier. Recess of the gate area of the barrier layer down to 6.3 nm significantly reduced the 2DEG density, brought the PC-HEMT to the "near threshold" operation and resulted in highly increased sensitivity. Thus, the specific 5-9 nm thickness of the barrier layer responsible for the pseudo-conducting behaviour of the PC-HEMT gives the sensor an incredible sensitivity.

In addition to the recessed or grown barrier layer thickness, roughness of the barrier layer surface is another very important parameter that has not been previously disclosed. It has been surprisingly found that that the roughness of the barrier layer surface bellow 0.2 nm prevents scattering of the donor-like surface trap states.

Figure 4A:
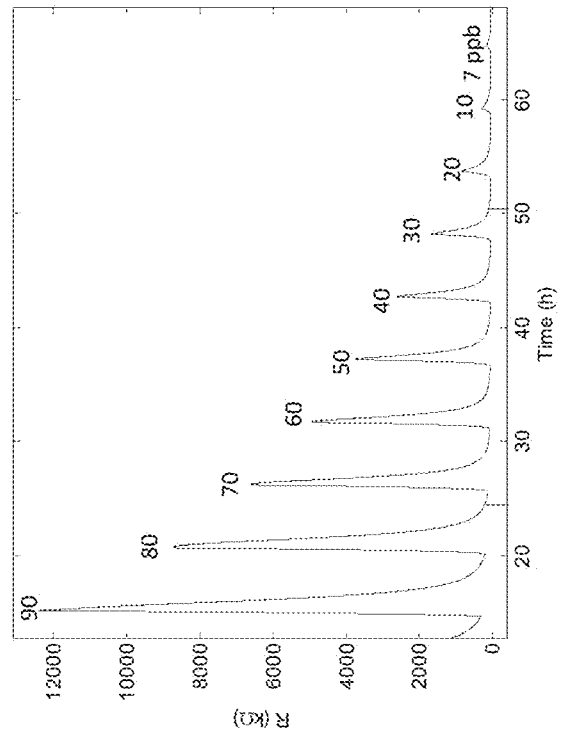
FIG. 4a shows sensitivity of the PC-HEMT for the 22-nm AlGaN barrier layer which is normally grown and then recessed to 6-7 nm.
Figure 4B:
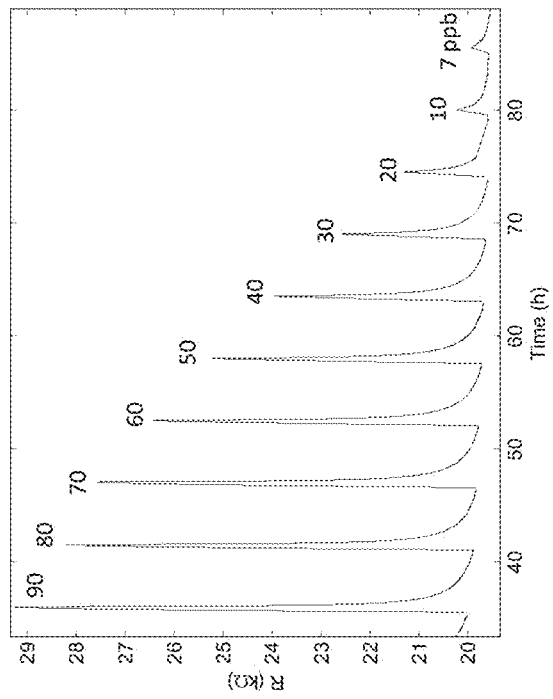
FIG. 4b shows sensitivity of the PC-HEMT for the ultrathin AlGaN barrier layer which is grown to 6-7 nm and then recessed down to 5-6 nm and etched with plasma.

FIG. 4a shows a decrease of electrical resistance for each treatment cycle with time for the 6-nm grown AlGaN barrier layer after short plasma activation (60 s). During this short plasma activation process, the AlGaN barrier layer is not recessed, but instead the 2-3-nm SiN layer (so called "GaN cap layer") is cracked and the surface states are ionised. FIG. 4b shows the same plot, but for the HEMT having the barrier layer recessed to 5-6 nm and treated with plasma (etched) for 450 s. The difference in sensitivity was found to be almost one thousand times in the favour of the recessed structure. In addition to the recessed or grown barrier layer thickness, roughness of the barrier layer surface is another very important parameter that has not been previously disclosed. It has been surprisingly found that that the roughness of the barrier layer surface (in the open gate sensitive area) bellow 0.2 nm prevents scattering of the donor-like surface trap states. Thus, the combination of these two features (5-9 nm thickness of the barrier layer in the open gate area and strongly reduced roughness of its surface) makes the PC-HEMT an incredibly strong functional amplifier.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN layers exhibit Ga-face positive polarity or N-face negative polarity. In other words, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:
Ga-Face Polarity
1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.
2) In another Ga-face configuration shown in FIG. 5a, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.
N-Face Polarity
3) The N-face polarity is characterised by the 2DEG formation in the top GaN layer above the AlGaN barrier layer, as shown in FIG. 5b. In this case, the AlGaN barrier layer and two GaN buffer layers must be nominally undoped or n-type doped.
4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example with Mg or Be as an acceptor) and the bottom GaN layer should be also p-type doped with Mg, Be or intrinsic.

Thus, there are four hetero-junction three-layer structures implemented in the transistor of the embodiments, based on the above configurations:
A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area or grown with this low thickness, with the roughness below 0.2 nm, and the thickness of the AlGaN barrier can be adjusted properly during growth.
B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).
C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm. Thickness of the AlGaN barrier can be adjusted during growth. N-type doping levels of the GaN buffer layer and the AlGaN barrier layer must be adjusted; the 2DEG has to be contacted (in the ideal case by ohmic contacts).

N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 5C:
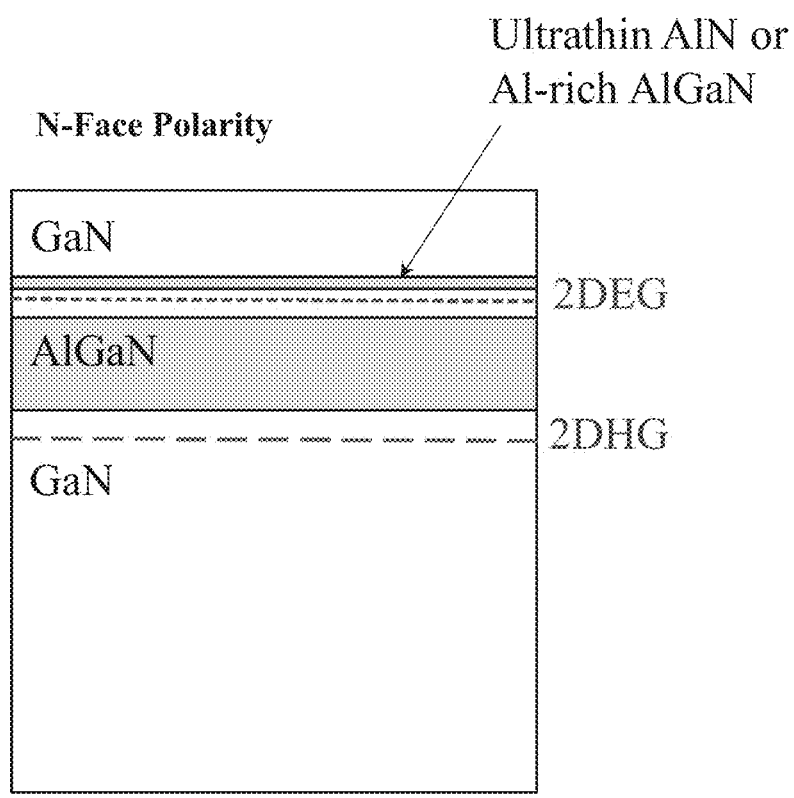
FIG. 5c schematically shows the formation of the 2DEG conducting channel in the N-face three-layer AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 5c, for the above "C" structure, it may be even more beneficial to include an ultrathin (about 1 nm) AN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

In order to solve the problem of the relatively slow response time of the biometric authentication sensor of an embodiment, an AC electrode (20) generating radio frequency (RF) square-sinus pulses is connected to the PC-HEMT as shown in FIGS. 1a-1b. It is defined as an "RF generator", because it emits specific frequency pulses in the range between 100 MHz to 100 GHz domain on the signal line through the body of a user using a microcontroller to switch between the AC pulse and the PC-HEMT sensing. The grounds of the RF generator and PC-HEMT are connected.

At proper frequencies the RF electromagnetic energy can be coupled into a human body. The cardio-pulmonary signals from the body of the user are then combined with the RF signals from the generator. These RF pulses sent to the body of a user may be internally "modified" by blood channels or other organs and tissues and reflected back to the PC-HEMT sensor. In other words, the AC pulsed signal may be modulated by the body's electrical fields and by various organs and tissue that would create a very unique "fingerprint" of the user. Since the interaction of the body with the RF radiation has a unique signature in terms of unique dielectric properties of each user, the RF emission into a body makes it possible to identify a unique body/RF-coupling signature instantly within a single second and express it using the cardio-pulmonary signals with very high resolution and high signal-to-noise ratio. The user may also use either finger or hand for authentication, which shows the clear advantage of this approach over the existing biometric techniques requiring the use of the same finger from the same hand each time. The existing biometric techniques using the capacitive sensors also have a problem of wet fingers or chapped fingers (for swimmers) or other environmental factors such as cold weather or heat, which is overcome by the sensor of the embodiments.

In another aspect of the present application, FIG. 6a shows a cross-sectional view of another configuration of the PC-HEMT of the present application with a radio-frequency generator (20) connected to the PC-HEMT, said PC-HEMT comprising:
- a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);
- a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts (15);
- the source and drain contacts (15) connected to said 2DEG or 2DHG conducting channel (13) and to electrical metallizations (14) for connecting said transistor to an electric circuit;
- a dielectric layer (16) deposited on top of the barrier layer (12) between said source and drain contacts (15); and
- a metal gate electrode (17) placed on said dielectric layer between said source and drain ohmic contacts (15) and electrically connected to a wire contact with any single body point.

In the above configuration, the barrier layer (12), specifically AlGaN layer, is not recessed, and the dielectric layer (16) of 1-10 nm thickness is deposited on the non-recessed barrier layer, followed by placing the metal gate electrode (17) on top of it. The metal gate electrode (17) thereby creates a hard mask for AlGaN recessing to the pseudo-conducting point and then exhibits a shadow gating effect to the open recessed areas. As a result, the charge trapping at the AlGaN/dielectric/metal interface is no longer affecting the recessed sensitive AlGaN area, and hence, the electrical leakage from the metal gate to the 2DEG channel is significantly decreased.

Figure 6B:
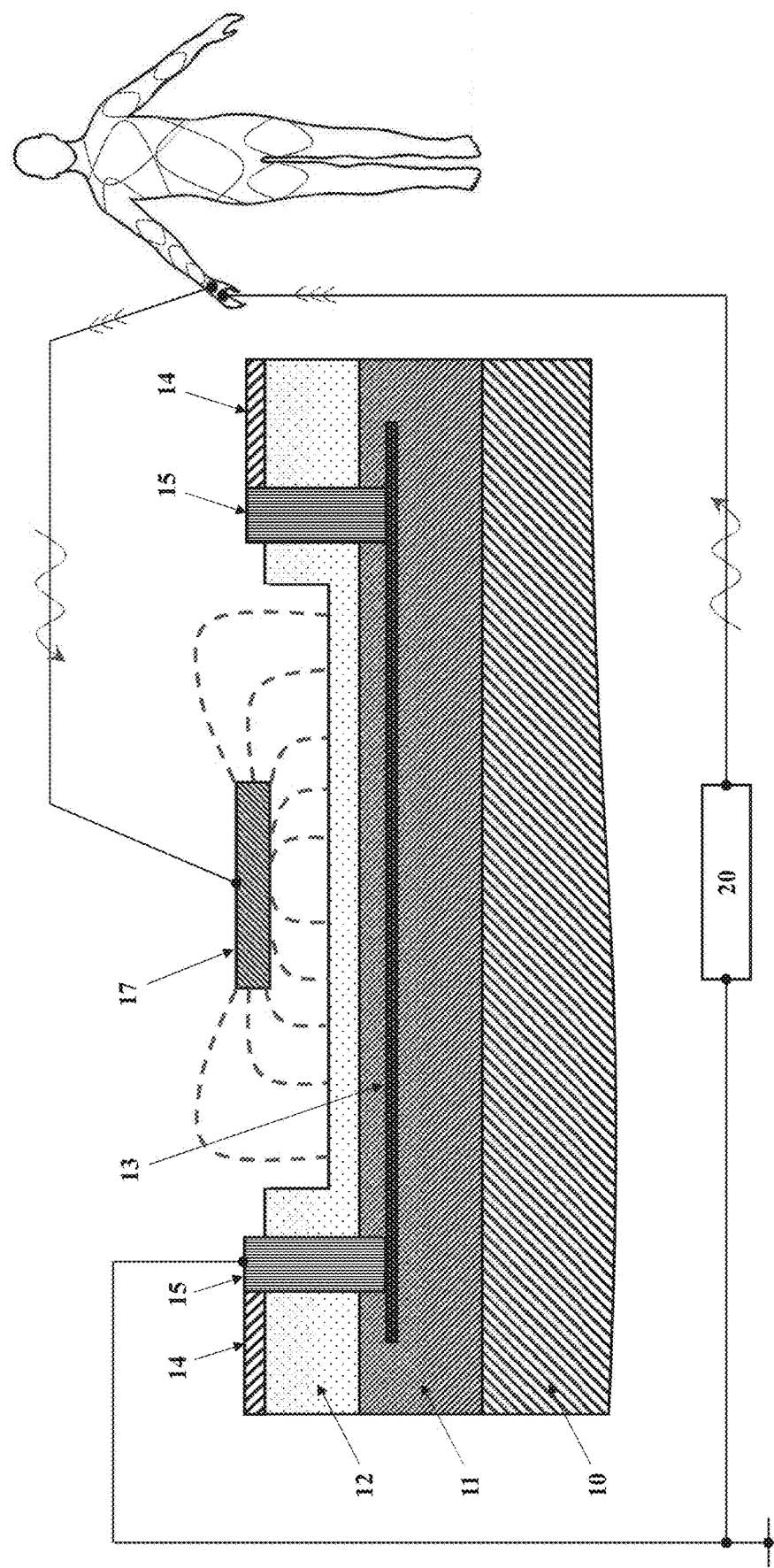
FIG. 6b shows a cross-sectional view of the PC-HEMT of an embodiment with a mechanically suspended metal gate and with an RF generator.

Further, FIG. 6b shows a cross-sectional view of still another configuration of the PC-HEMT of an embodiment of the present application comprising:
- a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);
- a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts (15);
- the source and drain contacts (15) connected to said 2DEG or 2DHG conducting channel (13) and to electrical metallizations (14) for connecting said transistor to an electric circuit;
- a mechanically suspended metal gate electrode (17) placed above the barrier layer (12) between said source and drain contacts (15) and electrically connected to a wire contact with any single body point;

wherein:
(i) the thickness (d) of said barrier layer (12) between said source and drain contacts (15) is about 5-9 nm which corresponds to the pseudo-conducting current range between normally-on and normally-off operation mode of the transistor;
(ii) the surface of said barrier layer (12) has a roughness of about 0.2 nm or less; and
(iii) said metal electrode (17) has no physical contact with said barrier layer (12) beneath.

In the above configuration, the metal gate of the transistor is realised as a mechanically suspended gate structure placed directly above the recessed barrier layer, at the height of about 10-100 nm. This configuration prevents any electrical leakage normally occurring at the metal gate/barrier layer interface. The suspended metal gate electrode (17) may be discharged from the parasitic charges via an additional opto-coupled electrode or using the AC-powered $V_{DS}$ and $V_{GS}$.

Figure 6C:
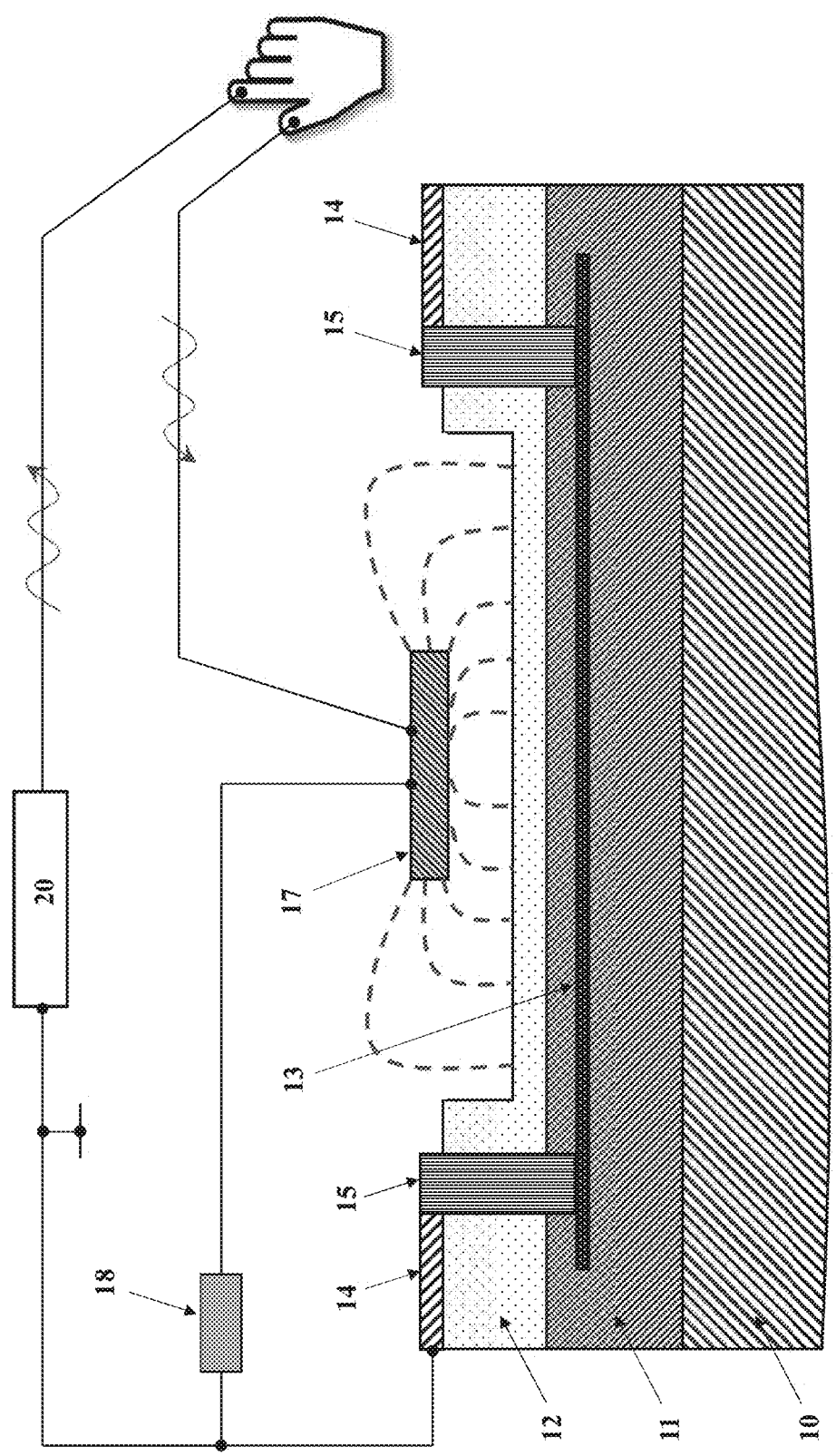
FIG. 6c shows a cross-sectional view of the PC-HEMT of an embodiment with a mechanically suspended metal gate being discharged via the connection to the source electrode and with an RF generator.

FIG. 6c shows a cross-sectional view of a slightly different configuration of the PC-HEMT of an embodiment of the present application, where the mechanically suspended gate electrode is discharged via the connection to the source electrode. This transistor comprises:
- a multilayer hetero-junction structure made of III-V single-crystalline or polycrystalline semiconductor materials, said structure comprising at least one buffer layer (11) and at least one barrier layer (12), said layers being stacked alternately, and said structure being deposited on a substrate layer (10);
- a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts (15);
- the source and drain contacts (15) connected to said 2DEG or 2DHG conducting channel (13) and to electrical metallizations (14) for connecting said transistor to an electric circuit;
- a mechanically suspended metal gate electrode (17) placed above the barrier layer (12) between said source and drain contacts (15) and electrically connected to said source contact and to a wire contact with any single body point;

wherein:
- (i) the thickness (d) of said barrier layer (12) between said source and drain contacts (15) is about 5-9 nm which corresponds to the pseudo-conducting current range between normally-on and normally-off operation mode of the transistor;
- (ii) the surface of said barrier layer (12) has a roughness of about 0.2 nm or less; and
- (iii) said metal electrode (17) has no physical contact with said barrier layer (12) beneath.

In the above configuration, the gate electrode is discharged via the connection to the source electrode. The connection can be high-ohmic and can be established via capacitor (18) to prevent the strong signal decay. In addition, the connection of the suspended gate to the source contact allows the fine tuning of the sensor gain by $V_{DS}$.

The source and drain contacts (15) in any of the above configurations may be either ohmic or non-ohmic contacts. For example, FIG. 7*a* shows a cross-sectional view of the PC-HEMT of an embodiment shown on FIG. 1*a*, but with non-ohmic source and drain contacts. In any of the configurations shown in FIGS. 1*a*-1*b* and 6*a*-6*c*, the ohmic source and drain contacts (15) may be replaced with the capacitively-coupled non-ohmic contacts resulting in the similar configurations with either the metal gate electrode placed over a dielectric layer in the non-recessed structure or with the suspended metal gate placed above the recessed barrier layer.

"Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conductive channel, they transfer more energy creating new high-energy vibrational states, thereby increasing resistance and temperature.

When electrical metallizations are placed over single-crystalline or polycrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semiconductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

If the source and drain contacts are non-ohmic (capacitively-coupled), in order to electrically contact the 2DEG channel, which is formed about 5-20 nm beneath the metallizations, the AC frequency regime should be used. The capacitive coupling of the non-ohmic metal contacts with the 2DEG channel is normally induced at the frequency higher than 30 kHz. In this case, the DC readout cannot be performed. Instead, the AC readout or impedance measurements of the electric current flowing through the conducting 2DEG channel are carried out.

FIG. 7*a* illustrates the situation when an electrical connection of the transistor to the 2DEG channel is realised via capacitive coupling to electrical metallizations through a Schottky barrier contact. This coupling becomes possible only if sufficiently high AC frequency, higher than 30 kHz, is applied to the metallizations. The electrical metallizations capacitively coupled to the 2DEG channel utilise the known phenomenon of energy transfer by displacement currents. These displacement currents are induced by existing electrical fields between the electrical metallizations and the conducting 2DEG channel operated in the AC frequency mode through the Schottky contact as explained above.

Reference is now made to FIG. 7*b* schematically showing a cross-sectional view of the PC-HEMT of an embodiment of the present application with highly-doped source and drain areas. In this case, the strong doping of the source and drain areas may result in a band-edge mismatch. However, if the semiconductor is doped strongly enough, it will form a potential barrier low enough for conducting electrons to have a high probability of tunnelling through, thereby conducting an electric current through the conducting 2DEG channel.

An electrical connection to the 2DEG channel shown in FIG. 7*b* is realised with a highly doped semiconductor areas

(19) overlapping the 2DEG channel and having a very low electrical resistance. Dopant ions such as boron (B$^+$), phosphorus (P$^+$) or arsenic (As$^+$) are generally created from a gas source, so that the purity of the source can be very high. When implanted in a semiconductor, each dopant atom creates a charge carrier in the semiconductor material after annealing. Holes are created for a p-type dopant, and electrons are created for an n-type dopant, modifying conductivity of the semiconductor in its vicinity. As$^+$ can be used for n-type doping, while B$^+$ and P$^+$ ions can be used for p-type doping. For example, in case of the AlGaN/GaN structure, the source and drain areas of the silicon structure are heavily doped with either B$^+$ or P$^+$ to create an electrical connection to the 2DEG channel. The silicon layers have a very low electrical junction resistance between each other in that case, and in order to induce an electrical current in the 2DEG channel, the metallizations are placed on top of the source and drain areas and connected to a circuit.

Figure 8A:
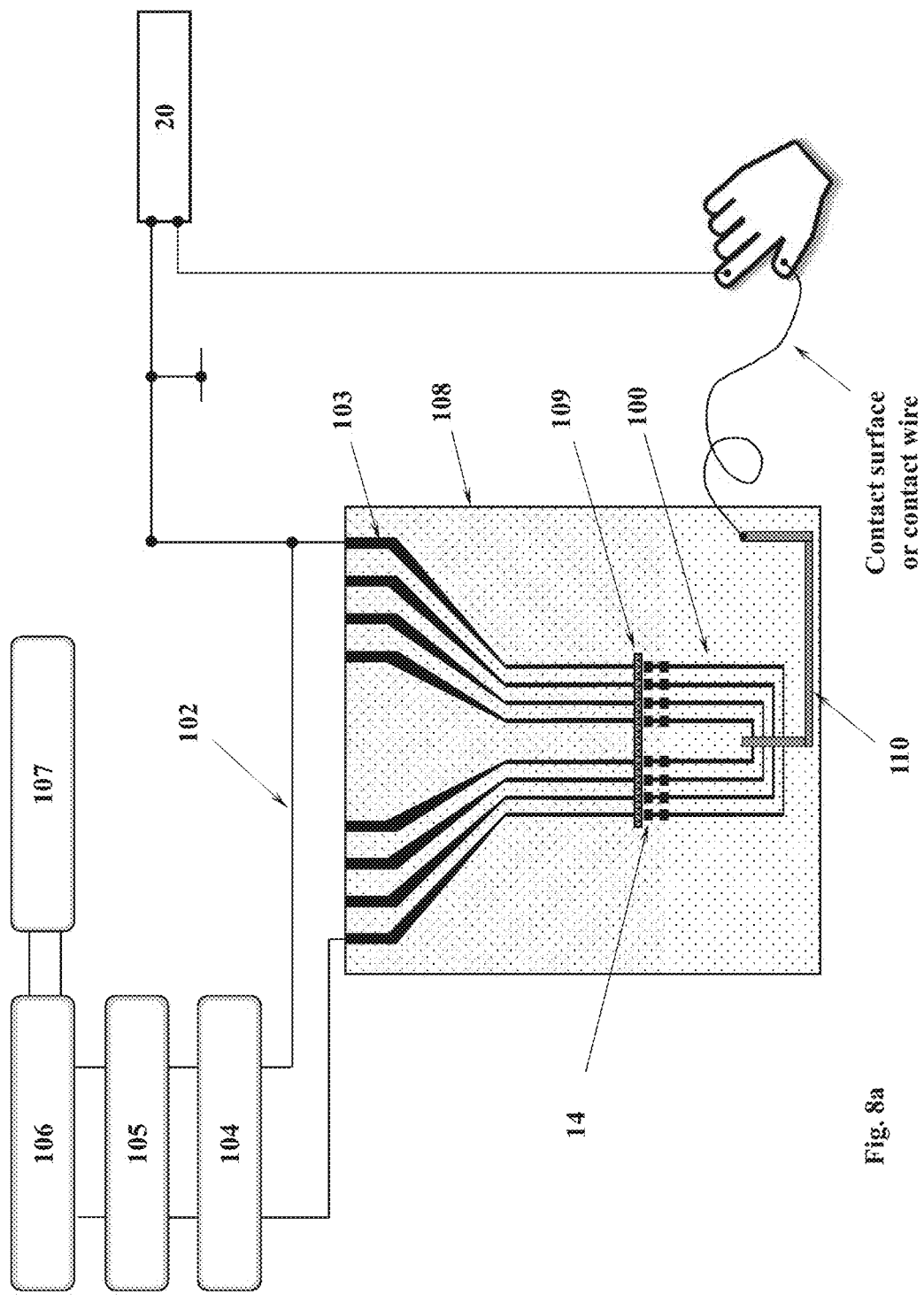
FIG. 8a schematically shows a PC-HEMT-based microelectronic sensor of an embodiment with a common suspended metal gate electrode and with an RF generator.

In another aspect of the present invention, FIG. 8a illustrates a microelectronic sensor comprising the following components:
- the PC-HEMT of an embodiment, or an array thereof (100), printed on a flexible printed circuit board (PCB) (108), wherein each one of said transistors is connected via electrical metallizations (14) to its dedicated electrical contact line (103) printed on said PCB (108);
- one common metal gate electrode (110) placed on said PC-HEMT or an array thereof (100), and electrically connected to a wire contact with any single body point;
- a voltage source (104) connected to said electrical contact lines (103) via an electric circuit (102) for supplying electric current to said transistors;
- an integrated or CMOS current amplifier (105) connected to said voltage source (104) for amplification of an electric current obtained from said transistors;
- an analogue-to-digital converter (ADC) with in-built digital input/output card (106) connected to said current amplifier (105) for outputting the converted signal to a user interface;
- a connection module (107) for connecting the sensor to the user interface; and
- a radio frequency generator (20) connected to said PC-HEMT or an array thereof (100) for emitting millisecond pulses to sample the body of a user.

As explained above, the RF generator (20) connected to the PC-HEMT and emitting millisecond pulses to sample the body, allows the AC signal to be modulated by the body and to detect the specific spectral fingerprint of the user in a single second with almost 100% identity. All the above components of the sensor can be external or built in the transistor. Each PC-HEMT of this sensor is fabricated on the substrate comprising 6-inch silicon wafers, the GaN buffer layer and the ultrathin grown AlGaN barrier layer, as described above. The AlGaN/GaN hetero-junction parameters used in this particular transistor were optimised for the ultrathin AlGaN barrier layer as follows: 3.5 nm SiN cap on top of the barrier layer, 6 nm $Al_{0.25}Ga_{0.75}N$ and 2 μm GaN buffer layer deposited on the Si wafer substrate. All the measurements further exemplified with this sensor were carried out on the fabricated samples without any additional surface treatment after ion implantation based 2DEG patterning step. The PC-HEMT element of the sensor may be placed within a packaging filled with 100% inert gas without any humidity.

The fabricated sensor is glued on the flexible fibro-plastic PCB (108), and its wire bond connectors are protected with epoxy-based glob-top (109). The voltage source (104) can be any suitable and commercially available battery of the Li-ion type or any energy harvester with AC-DC or DC-DC converters. The ADC card (106) is any suitable analogue-to-digital converter card that can be purchased, for example, from National Instruments® or LabJack®. The current amplifier (105) can be any commercially available femto-ampere amplifier, for example SRS® SR570, DLPVA-100-F-S, FEMTO® current amplifier DDPCA-300 or Texas Instruments® INA826EVM.

In a particular embodiment, the sensor is powered by a battery, such as an AA-battery. The connection module (107) can be an USB, a NFC or Bluetooth. There are two possibilities for the sensor setup operation including either a differential voltage amplifier connected in parallel, for example SRS® SR560, or a current amplifier connected in-line, for example a femtoamplifier SRS® SR570. The SR560 setup allows the operation in high input impedance mode using the voltage divider resistance R. The relatively high SR560 input resistance of 100 MΩ is good for detection of very small charges without big leakages.

Another setup includes a current amplifier that operates directly with current flowing via the 2DEG channel of the PC-HEMT into the amplifier with small input resistance of 1 MΩ at gain higher than $10^4$ and only 1Ω at gains lower than 200. Since the current amplifier in this case is switched off, the usage of voltage divider R is not necessary unless the voltage of 1.6V from the AA-element is too high. Thus, this setup directly amplifies the electric current modulation in the 2DEG channel originated from an external body charges. All readout components are battery powered to avoid ground loop parasitic current.

Figure 8B:
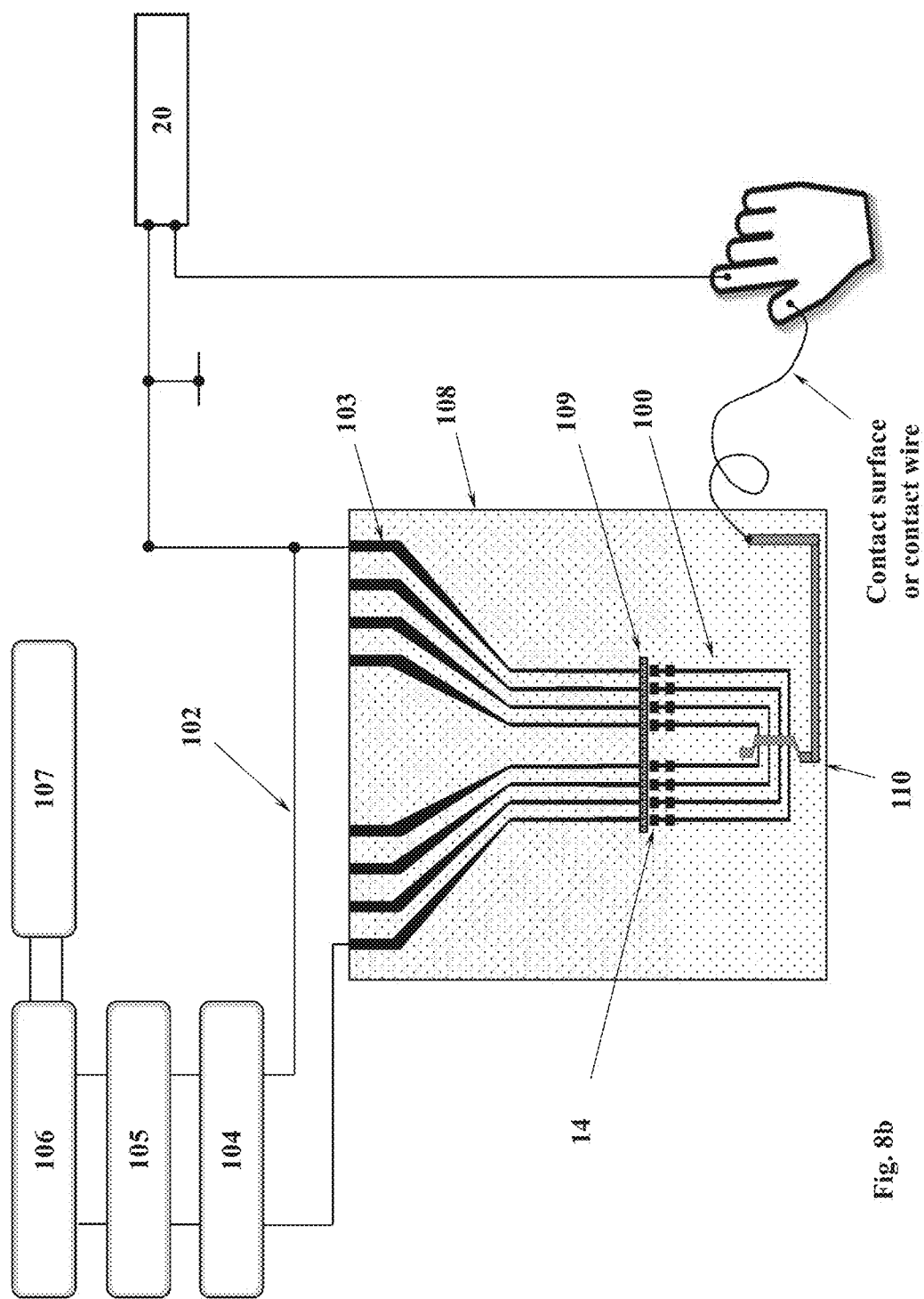
FIG. 8b schematically shows a PC-HEMT-based microelectronic sensor of an embodiment with a common mechanically suspended metal gate electrode, which has no physical contact with the PC-HEMT or array thereof.

In a further embodiment, the sensor shown in FIG. 8b contains a common suspended metal gate electrode (110), which has no physical contact with the PC-HEMT or array thereof (100). The metal gate electrode (110) in this case is placed directly above the PC-HEMT or array thereof (100), at the height of 10-100 nm. This configuration prevents any electrical leakage normally occurring at the metal gate/barrier layer interface.

Figure 9:
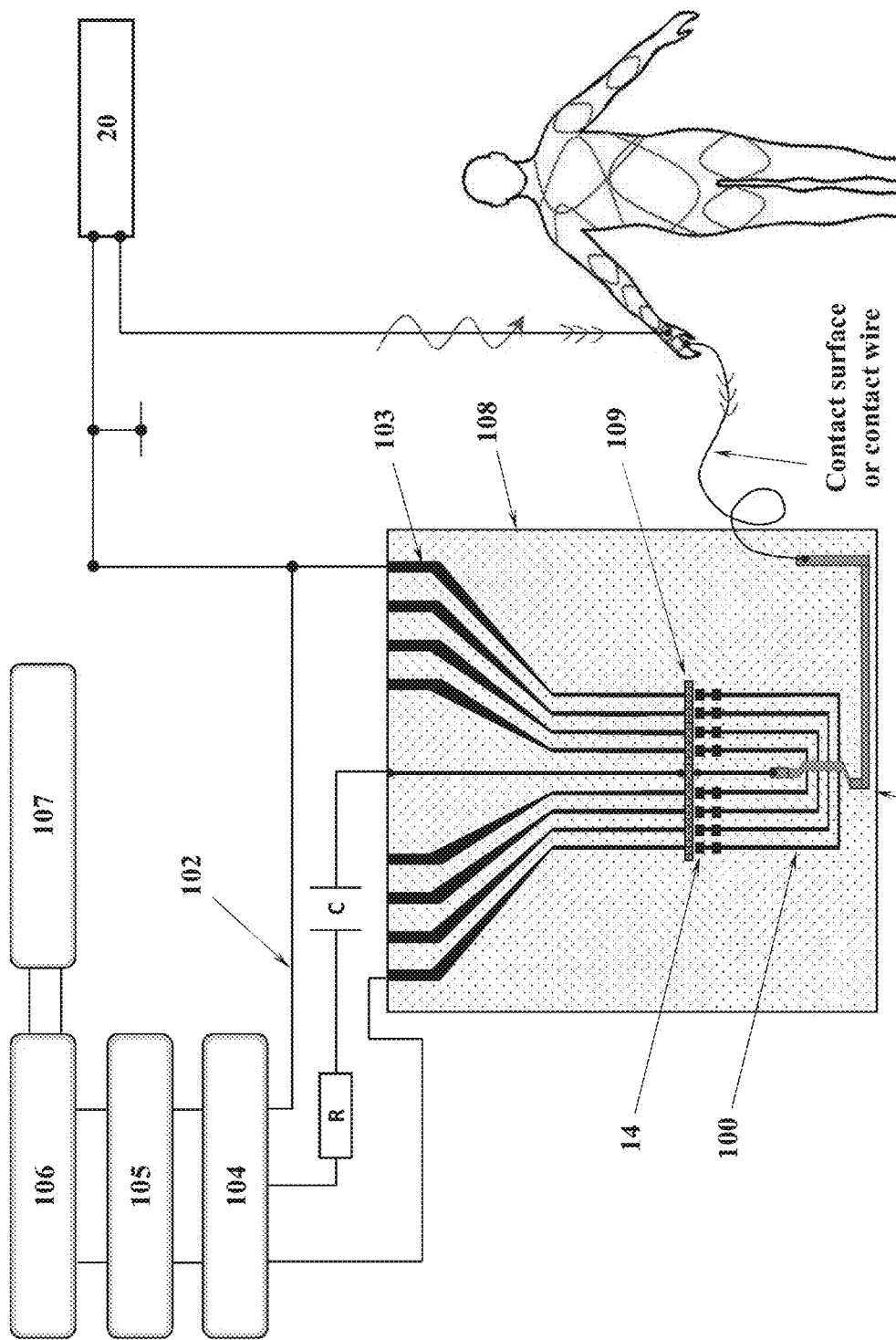
FIG. 9 schematically shows a PC-HEMT-based microelectronic sensor of an embodiment with a common metal gate electrode placed in contact with the PC-HEMT or array thereof and discharged via the connection to a source electrode.

FIG. 9 shows the sensor where either the mechanically suspended metal gate electrode or the metal gate electrode placed in contact with the transistors is discharged via the connection to the source electrode. The connection can be high-ohmic and can be established via capacitor to prevent the strong signal decay.

The third option would be the use of the photoeffect that may also induce an electric current in the 2DEG channel. In order to couple the light excitation with the electronic effects in the conducting 2DEG channel, a photoeffect in a silicon layer should be created. Regarding the direct photoeffect, it is well known that light can only be absorbed when the energy of the absorbed photon (E=hv) is large enough for an electron to be excited into the valence band. In that case, E is the photon energy, h is Planck's constant and v is the frequency of the photon. The frequency is coupled to the wavelength λ of light by the constant speed of light c=λv. Typically the bandgap of silicon at room temperature is 1.12.eV, which means that silicon becomes transparent for wavelength larger than 1240 nm, which is the near infrared range.

For smaller wavelength (i.e. larger energy of the photons), electron/hole pairs are generated leading to a photocurrent. In the fully-depleted, intrinsically doped silicon structures, this results in a higher charge carrier density and consequently, higher sensitivity. For these structures, light is adsorbed in the whole visible range making such devices ideal photodetectors. The mechanism that allows the silicon semiconductor to become photosensitive to irradiation with light has already been described in literature. In the direct photoeffect, it can be tuned by the size, crystalline direction and surface termination. These effects originate from two-dimensional quantum confinement of electrons in the nano-sized 2DEG structure.

Although irradiation of the silicon structure with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed (see the definition and explanation of the surface trap states below). The electrons actually deplete the holes trapped at the surface and hence, modulate the gate field. The photogenerated holes are confined to the centre of the silicon structure by the gate field, where they increase the conduction of the 2DEG channel, because of the band bending. The holes increase the channel conductivity for a certain lifetime until they are trapped (recaptured) at the surface. The gain of the transistor can be extremely huge if this re-trapping lifetime is much longer than the holes transit time.

All the aforementioned PC-HEMT configurations may further comprise an electro-optical (EO) crystalline material, such as lithium niobate (LiNbO) or lithium tantalite (LiTaO$_3$), which is brought into a physical contact with a human skin at any single body point. In other words, the sensor of an embodiment, may be based on a piezoelectric electro-optical crystal transducer (EOC) combined with the pseudo-conducting 2DEG-based structure. The sensor based on the EOC piezoelectric substrate exhibits the highest coupling between electrical and mechanical energy compared to all other varieties of substrates. Additionally, such substrate also has the advantages of having a high velocity-shift coefficient and a very high electromechanical coupling coefficient, K2, which yields a greater mass sensitivity in comparison with the regular sound-acoustic wave (SAW) device on any other piezoelectric substrates. As mentioned above, the EOC may be any suitable electro-optical crystalline material such as LiNbO$_3$, which is brought into a physical contact with a single point on a user's body. The EOC is then illuminated with an excitation light beam of polarised light, In case of the LiNbO$_3$ crystalline material, the wavelength of the polarised light is about 400-600 nm, as mentioned above. Modulated light from the light source illuminates the EOC, and then falls on the 2DEG-based structure. As explained above, the 2DEG-based structure is ultrasensitive to an incident light, which creates p-n-pairs in the AlGaN barrier layer, and consequently, strongly affects the 2DEG-conductivity. Irradiation of the 2DEG-based structure with light switches the 2DEG-channel from normally-off to a pseudo-conducting or normally-on state. In general, in the ultrasensitive state of the PC-HEMT, a very small number of photons can switch the 2DEG channel from a normally-off mode to a normally-on mode resulting in a strong pseudo-conducting behaviour of the PC-HEMT, which increases the sensitivity of the transistor at least three orders of magnitude. Therefore, by contact with the body of a user (or with an electrical charge of the body), the EOC may modulate its light absorbance, thus strongly affecting the electrical current flow in the 2DEG channel and thereby resolving any tiniest intensity changes of the excitation light transferred through the EO crystal.

Because the hemodynamic signals recorded by the PC-HEMT are relatively slow, the PC-HEMT is able to sense and record all the hemodynamics of the body. Using the PC-HEMT of the embodiments with the integrated EOC makes it possible to fully decouple the conducting 2DEG structure from any parasitic electrical charge coming from the human body. Depending on the excitation light wavelength, the position of the sensor relative to the incident light beam can be adjusted accordingly. For example, in case of the IR light, which has the wavelength range of about 700-1500 nm, the sensor should be placed perpendicularly to the light beam for achieving the highest sensitivity. The parasitic charging of the EOC may be compensated via the electrodes attached to the crystal. Additionally, the PC-HEMT may be combined with a variety of light filters placed in front of the PC-HEMT to achieve a particular wavelength of excitation.

Figure 10:
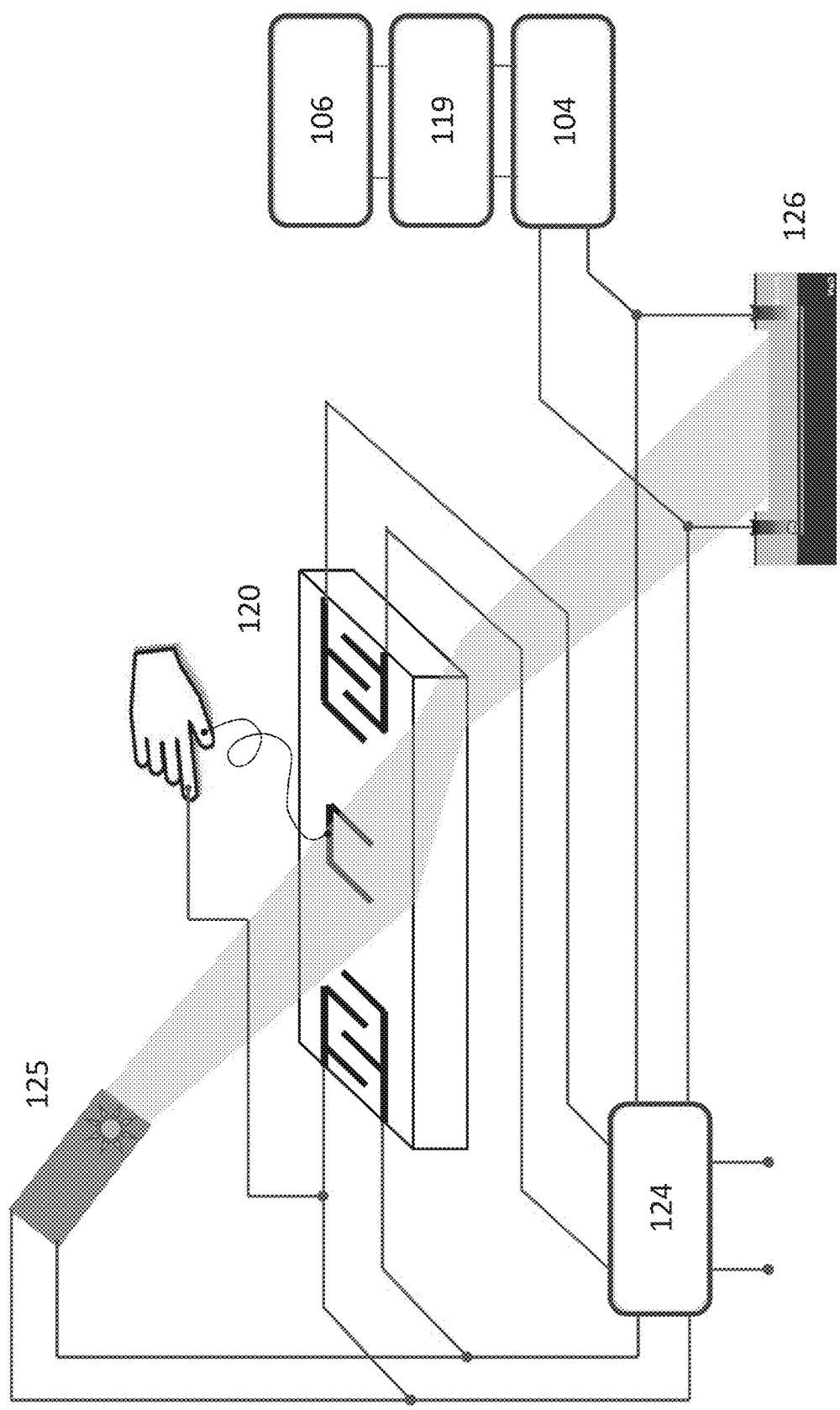
FIG. 10 schematically shows an optoelectronic sensor of an embodiment.

In still another embodiment, FIG. 10 schematically shows an optoelectronic sensing device of an embodiment, for material and structure sensing, with a remote readout comprising the following components:

a sound-acoustic wave (SAW) sensor chip (120) connected via ohmic contacts to an electric circuit;

a modulated light source (125), such as a surface-mounted-device light-emitting diode (SMD LED) or UV-VIS-IR laser diode, for irradiating the AlGaN barrier layer surface of the pseudo-conducting 2DEG structure (126) on the sensor chip;

optocoupler switches (124) for coupling said modulated light source (125) with said pseudo-conducting 2DEG structure (126) on the sensor chip;

a voltage source (104) connected to said electrical circuit for supplying electric current to said SAW sensor chip (120);

a lock-in amplifier (119) connected to said voltage source (104) for amplification of a signal with a known carrier wave obtained from said SAW sensor chip and increasing the signal-to-noise ratio;

an analogue-to-digital converter (ADC) with in-built digital input/output card (106) connected to said lock-in amplifier (119) for outputting the converted signal to a user interface; and a radio frequency generator (20) connected to said SAW sensor chip (100) for emitting millisecond pulses to sample the body of a user.

Thus, the use of the SAW-EOC configuration makes it possible to drastically increase the sensitivity of the sensor to an electrical charge, to discharge the EOC via the SAW-based charge transport along the crystal surface, to efficiently modulate polarised light from the light source and to control the SAW delay line effect with the phase velocity signal. The opto-coupler switches (124) couples the pseudo-conducting 2DEG-based structure (126) with the SAW-EOC such that the initial SAW actuation signals at the emitter (left) IDT electrodes are synchronised with the modulated light source (125) and with the $V_{DS}$ at the pseudo-conducting 2DEG-based structure. A signal at the receiver (right) IDT electrodes is coupled back to the $V_{DS}$ via the opto-coupler (124), which is brought into a resonance with initial signals and with the light source (125) modulation. Due to a physical galvanic connection of the SAW-EOC with the body single point by spatially patterned electrodes, the EOC changes its light absorption and modulation properties. This strongly affects the resonant mode of the five initial signal sources ($V_{DS}$, emitter IDT, light source, receiver IDT and SAW-modulated light source). Thus, because of the light source-based interaction, the resonant system becomes very stable and also very sensitive to external charges.

Two co-pending patent application U.S. Ser. No. 15/157,285, from which the present application claims priority, and PCT/IB2017/051320, by the same applicant, exemplifies different types of hemodynamic and cardio-pulmonary data recorded on a single point of a patient's body. This data comprises heart rate variability (HRV), breath rate dynamics, central venous pressure (CVP), left and right atrium pressures (LAP and RAP), as well as the ECG data. In addition, the physiological S2 split sound dynamics data associated with phonocardiogram and recorded with the PC-HEMT sensor is also described therein.

Figure 11B:
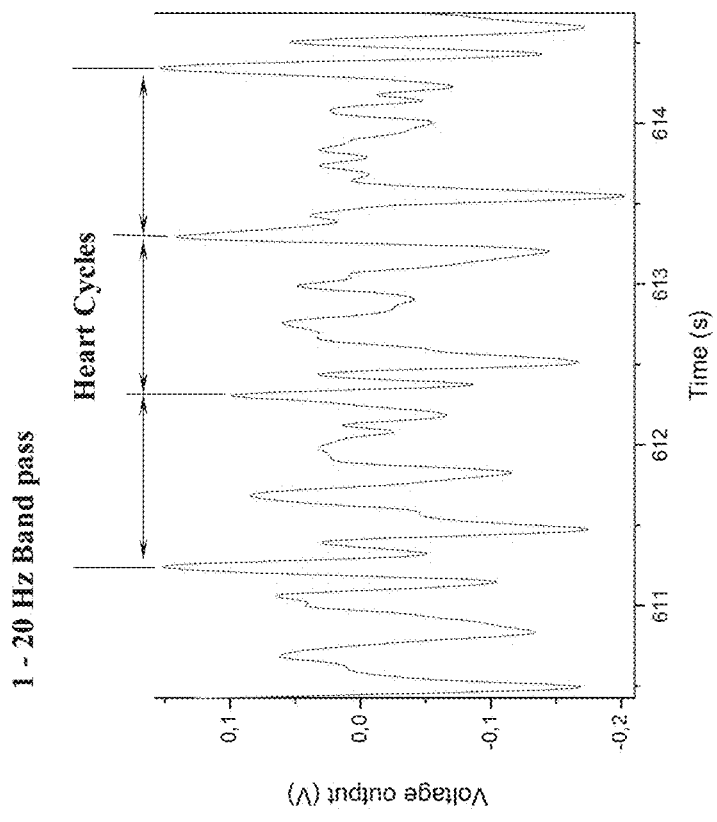
FIG. 11b shows the cardio-pulmonary hemodynamic data recorded with the sensor of an embodiment for User 1 with the 1-20 Hz band-pass filter.
Figure 11A:
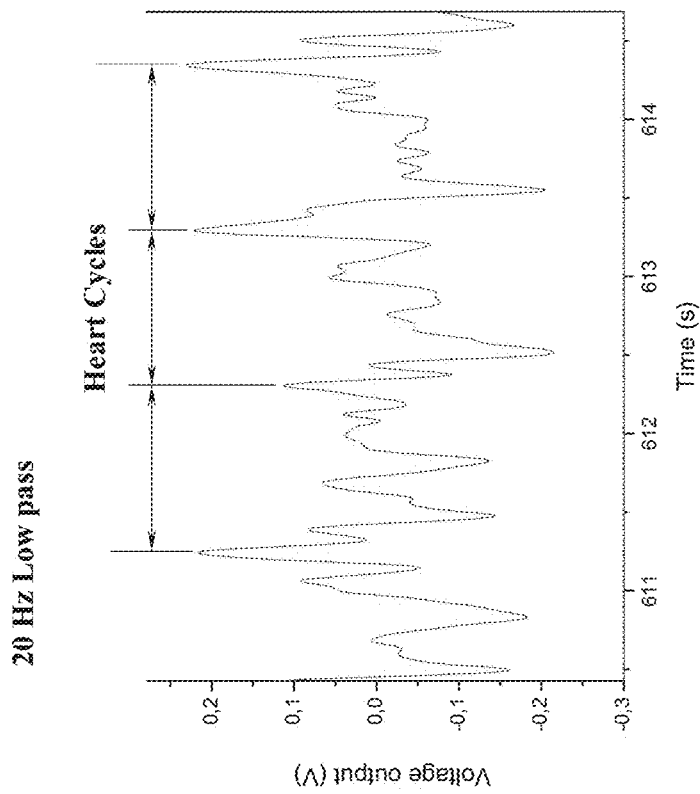
FIG. 11a shows the cardio-pulmonary hemodynamic data recorded with the sensor of an embodiment for User 1 with the 20 Hz low-pass filter.
Figures 11C, 11D:
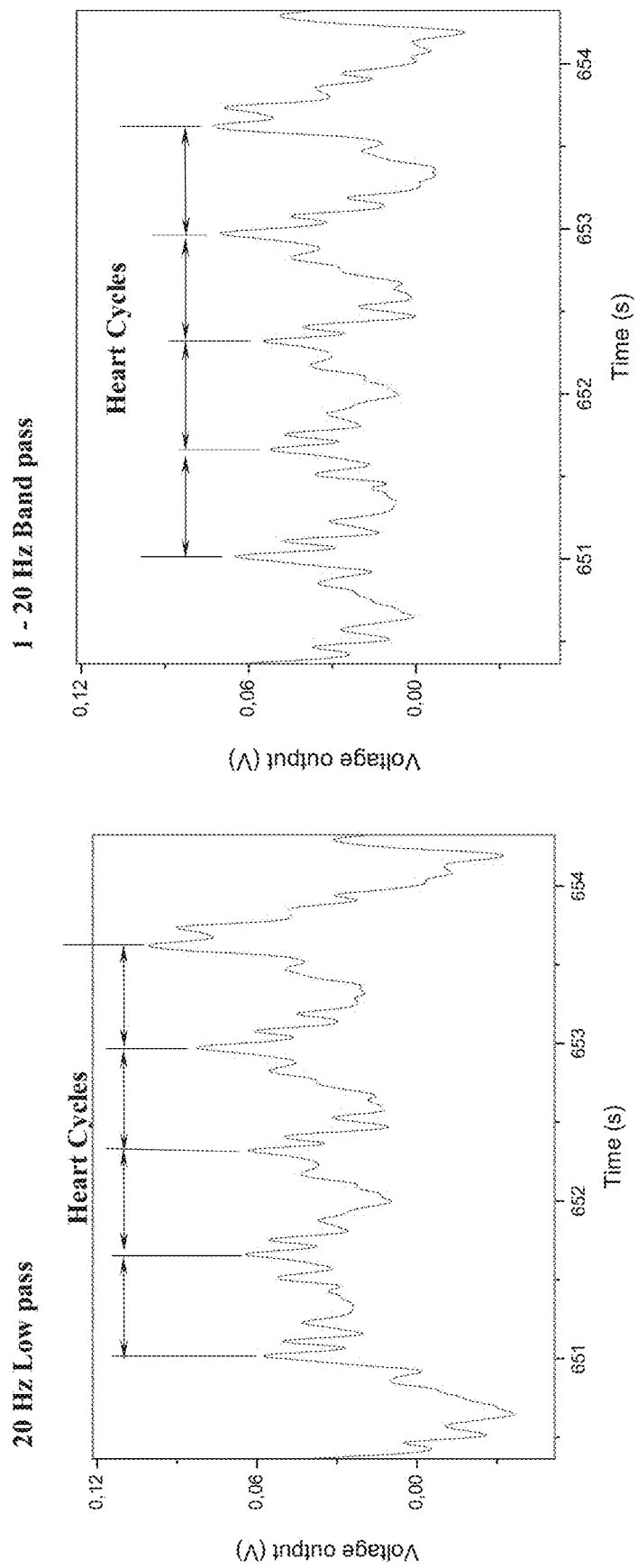
FIG. 11c shows the cardio-pulmonary hemodynamic data recorded with the sensor of an embodiment for User 2 with the 20 Hz low-pass filter.
FIG. 11d shows the cardio-pulmonary hemodynamic data recorded with the sensor of an embodiment for User 2 with the 1-20 Hz band-pass filter.
Figure 11F:
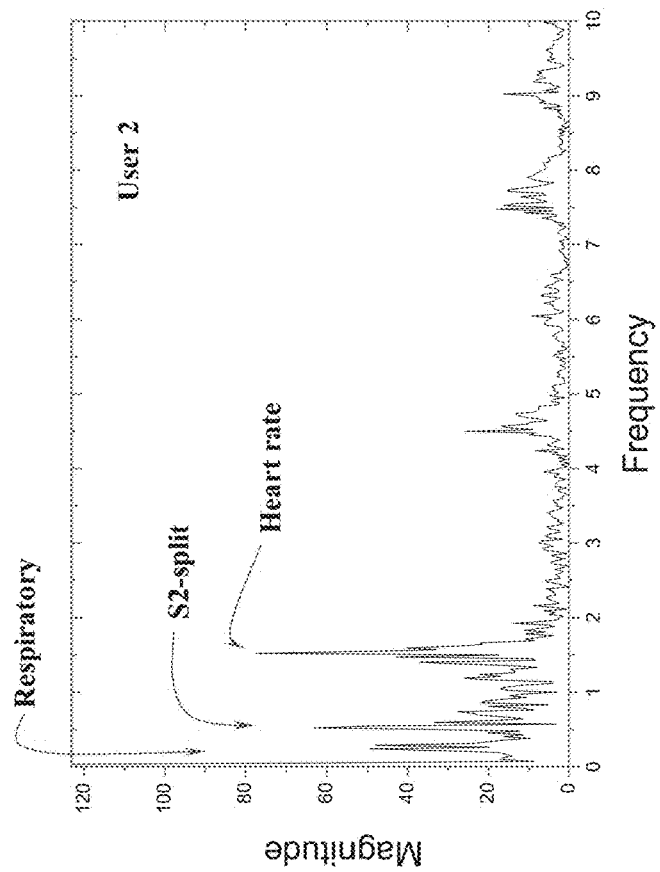
FIGS. 11e-11f show the ID FFT spectra calculated for User 1 and User 2.
Figure 11E:
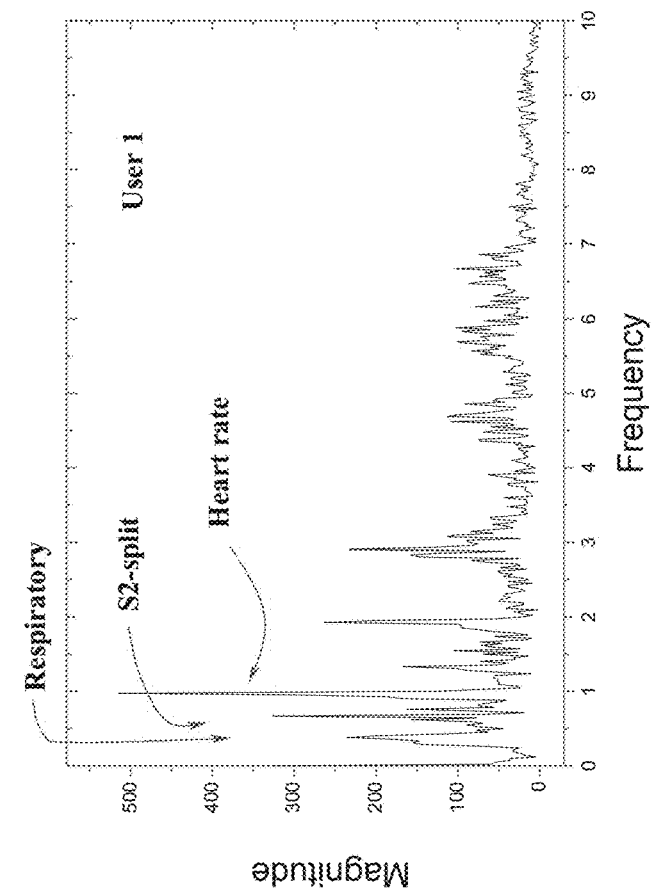
Figure 11H:
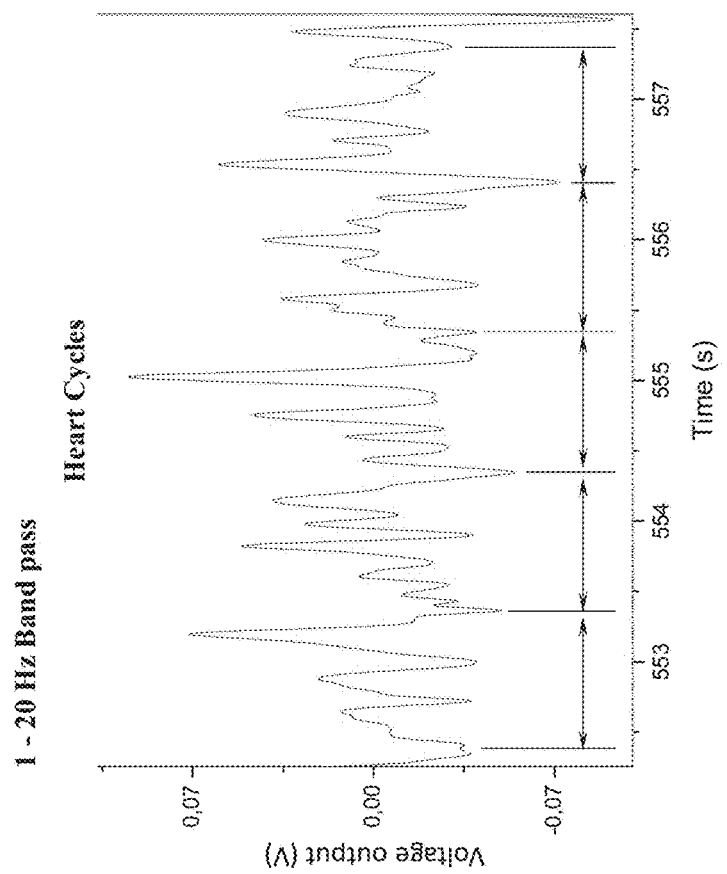
FIG. 11h shows the cardio-pulmonary hemodynamic data recorded with the sensor of an embodiment for User 3 with the 1-20 Hz band-pass filter.
Figure 11G:
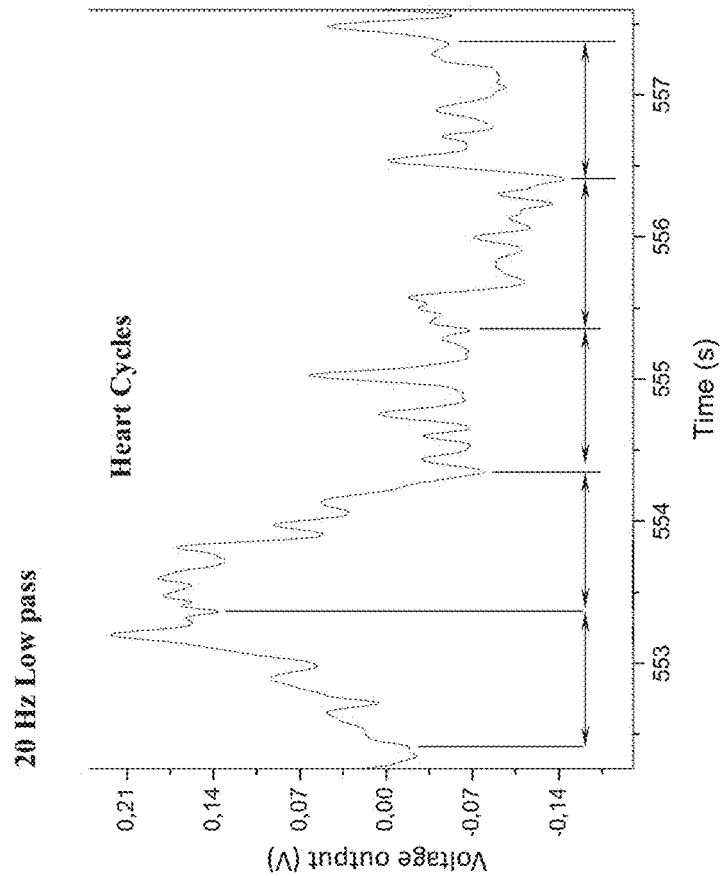
FIG. 11g shows the cardio-pulmonary hemodynamic data recorded with the sensor of an embodiment for User 3 with the 20 Hz low-pass filter.
Figures 11I, 11J:
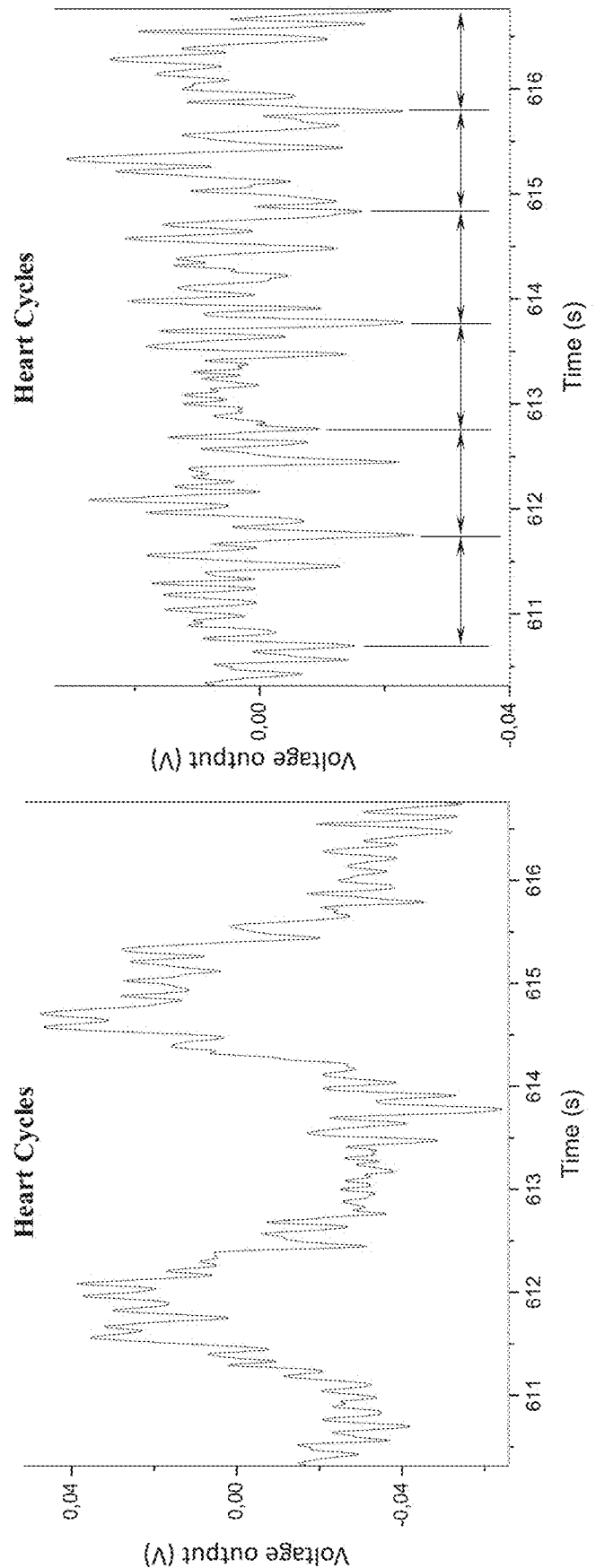
FIG. 11i shows the cardio-pulmonary hemodynamic data recorded with the sensor of an embodiment for User 4 with the 20 Hz low-pass filter.
FIG. 11j shows the cardio-pulmonary hemodynamic data recorded with the sensor of an embodiment for User 4 with the 1-20 Hz band-pass filter.
Figure 11L:
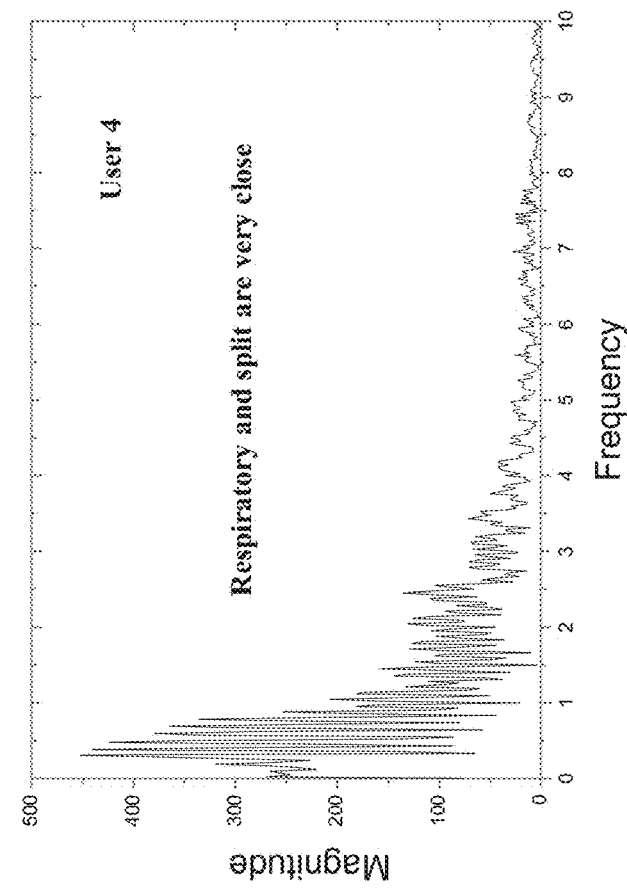
FIGS. 11k-11l show the ID FFT spectra calculated for User 3 and User 4.
Figure 11K:
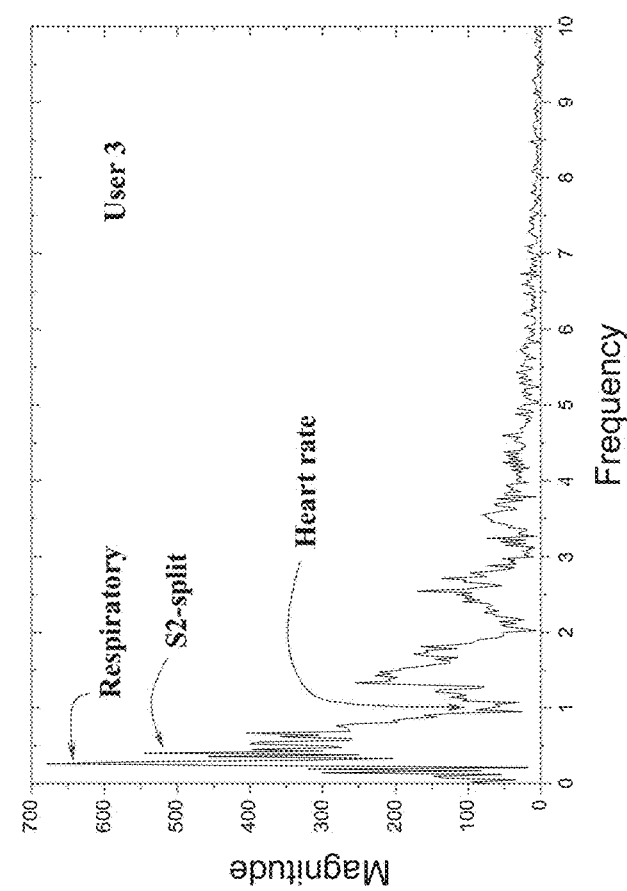
Figure 11M:
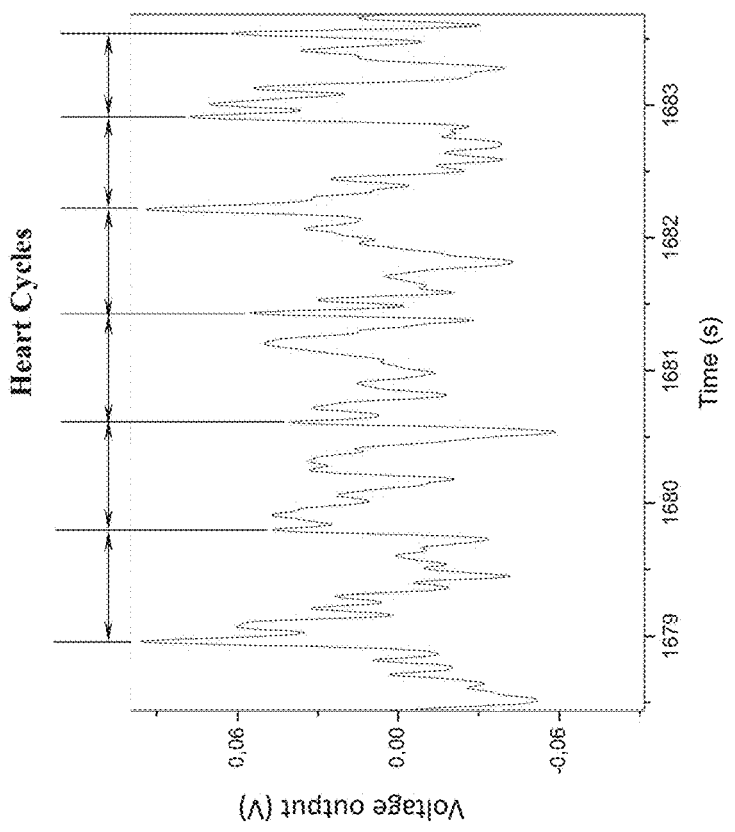
Figure 11M:
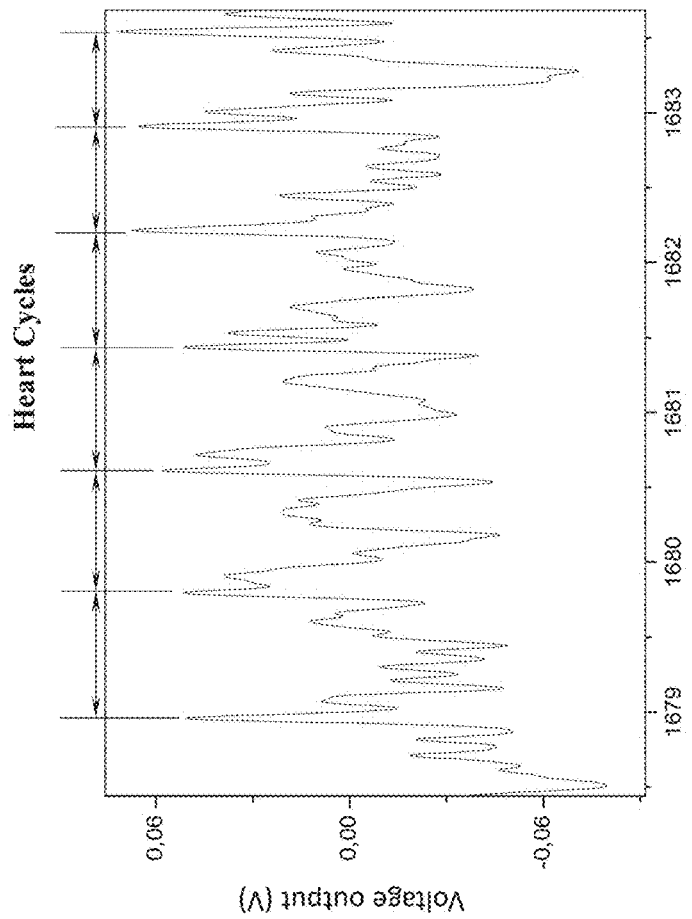
Figure 11O:
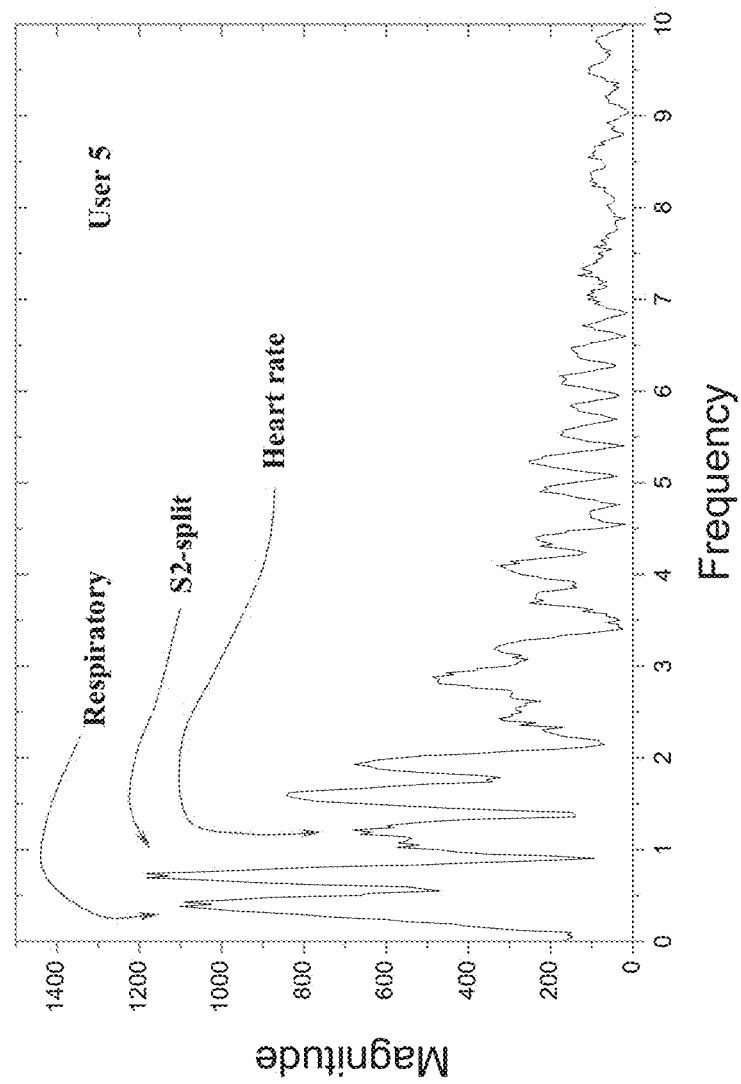
FIG. 11o shows the ID FFT spectra calculated for User 5.
Figure 12B:
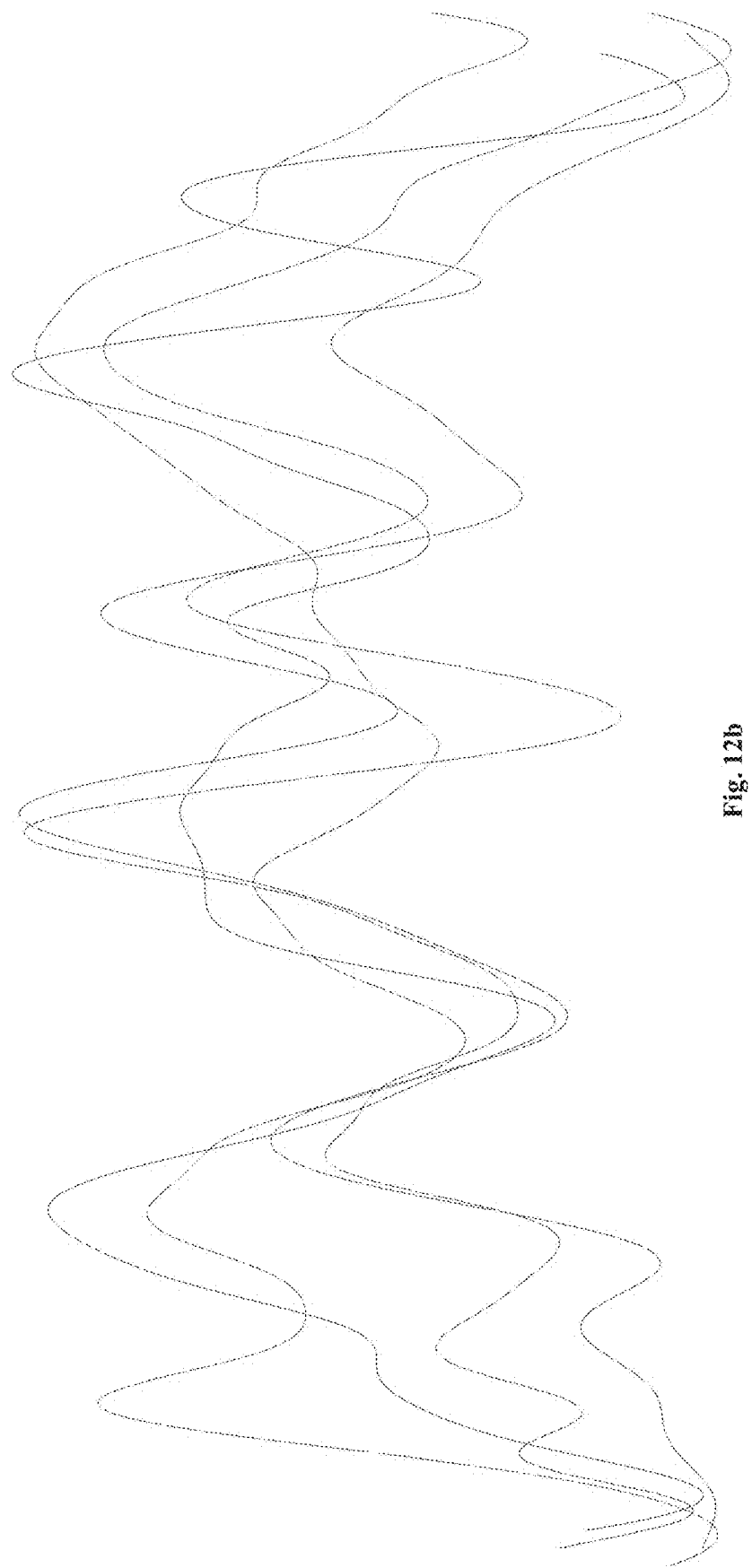
FIG. 12b shows the heart cycles of the five different users normalised on a time and amplitude scale.

In an embodiment of the present application, the combination of the above cardio-pulmonary hemodynamic data is used for personal biometric authentication as demonstrated in the following examples. FIGS. 11a-11o exemplify the cardio-pulmonary hemodynamic data (heart rate RAP ID-pattern) recorded with the PC-HEMT sensor for five different users. FIG. 12a shows the single heart cycles extracted from the above data for the five persons, while FIG. 12b shows these heart cycles normalised on a time and amplitude scale. It is clear from these experimental results that the biometric data recorded with the sensor of an embodiment of the present application is a true "body organs fingerprint" of a particular person, which is unique for this particular person. Some people may have absolutely different biometric signatures recorded with the PC-HEMT sensor of embodiments, while some persons may demonstrate slightly similar biometric signature, but it can never be the same. Therefore, based on the individual data recorded with the PC-HEM sensor, the high precision personal authentication method can be used in many different gadgets and devices, where the PC-HEMT sensor is integrated.

The biometric authentication method based on the PC-HEMT sensor is much more precise and more secure compared to the ECG based biometric authentication. The biometric data recorded with the PC-HEMT contains the CVP-RAP hemodynamics of the heart muscle movements due to a polarisation wave. The shape and dynamics of the heart for each person is unique, and the dynamics of the right and left atriums within the heart significantly differs from person to person. In combination with the S2-split data originated from a heart-lung disposition and interaction, the unique signature of a person becomes at least ten times more precise than the ECG signature. The phenomenon behind this is that the S2-split does not occur at apex of the breath peaks, but it is always present with its maximum effect at the inhaling apex. This means that the hemodynamic data recorded with the PC-HEMT sensor is continuously modulated via the superposition of the lungs/heart activities, and it depends on the location of the heart relative to the lungs, as well as their interaction dynamics. The ECG data is actually contained within the "body organs fingerprint" recorded with the PC-HEMT sensor.

In some embodiments, the PC-HEMT sensor of the invention may be integrated within a smartwatch, smartphone or in any other available personal gadget, including but not limited to a bracelet, a ring or an earring, with or without any direct skin-contact to the sensor interface. It can be connected to the metallic chassis or to the capacitive sensitive display elements of the smartphone transducing an electrical charge to the sensor. The PC-HEMT sensor may replace the fingerprint sensor within the smartphone lock. The in-built PC-HEMT sensor is capable of sensing the signals and transmitting them either to a smartphone or directly to a biometric authentication cloud. The biometric authentication can be continuously carried out when the sensor is in a contact with a body or activated on calling or when the contact is established. The relevant biometric data recorded is then transmitted to a biometric authentication cloud and will be available for further processing. It can be also used in an automotive sector with car locks and bio-vital hemodynamic monitoring of the driver (sleepiness, cardio, stress etc.)

In a certain aspect, a wearable device of the present application contains an integrated PC-HEMT sensor comprising the following components:
the PC-HEMT of an embodiment, or an array thereof, wherein each one of said transistors is connected to its dedicated electrical contact line;
a battery connected to said electrical contact lines via an electric circuit for supplying electric current to said transistors;
an integrated or CMOS current amplifier connected to said battery for amplification of an electric current obtained from said transistors;
an analogue-to-digital converter (ADC) with in-built digital input/output card connected to said current amplifier for wirelessly outputting the converted signal to a smartphone or to an authentication cloud;
a wireless connection module for wireless connection of said wearable device to a smartphone or to an authentication or medical-diagnostic telemedicine cloud; and
a radio frequency generator connected to said PC-HEMT of an embodiment, or an array thereof, for emitting a radio frequency signal in a form of millisecond pulses to sample the body of a user.

In a specific embodiment, the wireless connection module can be a short-range Bluetooth or NFC providing wireless communication between the wearable device and a smartphone for up to 20 m. If this module is WiFi, the connection can be established for up to 200 nm, while GSM allows the worldwide communication to a medical-diagnostic telemedicine cloud.

In some embodiments, the wearable device of and the system of the present application can be used for portable long-time-operation solution within a biometric authentication cloud. Since the biometric device is continuously used by a wearer, it should have a very small power consumption saving the battery life for a prolong usage. This is one of the major reasons to preferably use the non-ohmic high-resistive contacts connecting the PC-HEMT sensor to an electric circuit (this sensor configurations shown in FIG. 7). The non-ohmic contacts actually limit an electric current flowing through the 2DEG channel by having an electrical resistance 3-4 times higher than the resistance of the 2DEG-channel, thereby reducing electrical power consumption without sacrificing sensitivity and functionality of the sensor. Thus, the use of non-ohmic contacts in some embodiments of the PC-HEMT sensor of the present application is a hardware solution allowing minimising the power consumption of the device. In another embodiment, the power consumption of the device can be minimised using a software algorithm managing the necessary recording time of the sensor and a battery saver mode, which limits the background data and switches the wireless connection only when it is needed.

Figure 13:
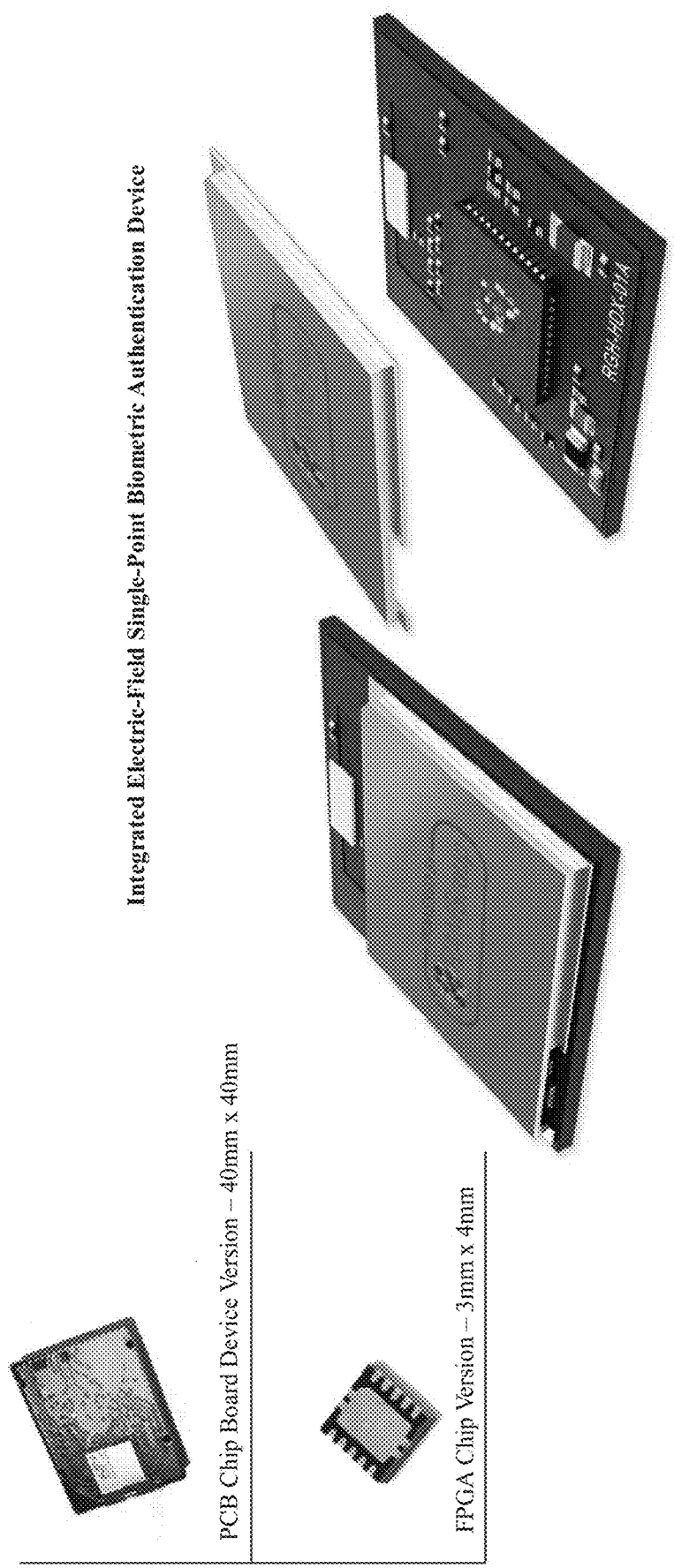
FIG. 13 shows a prototype of the biometric authentication device based on the sensor of an embodiment.

FIG. 13 demonstrates a prototype of the biometric authentication device based on the PC-HEMT sensor of the present application. In a particular embodiment, a method for biometric authentication of a user comprises the following steps:
1) Contacting a single sensing point on a user's body with the microelectronic sensor of the embodiments, or activating said sensor on calling or when the contact is established;

2) Emitting a radio-frequency signal in a form of millisecond AC pulses with said microelectronic sensor into a body of the user;
3) Recording electrical signals together with the reflected AC signal, modulated in a body of the user, received from said single point on the user's body in a form of a source-drain electric current of the transistor (defined as $I_{DS}$ dynamics);
4) Transmitting the recorded signals to a smartphone, smartwatch or to any other available personal gadget or mobile device, to a desktop computer, server, remote storage, internet storage or to a biometric authentication cloud for further processing; and
5) Processing the transmitted signals, correlating and comparing said $I_{DS}$ dynamics with the pre-calibrated and stored biometric data of the user, thereby biometrically authenticating the user.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A biometric authentication device for biometric authentication of a user comprising a microelectronic sensor comprising
    (1) an open-gate pseudo-conductive high-electron mobility transistor or an array thereof capable of sensing electrical signals produced by a body of the user, wherein said transistor comprises:
        a) a multilayer hetero-junction structure made of gallium nitride (GaN) and aluminium gallium nitride (AlGaN) single-crystalline or polycrystalline semiconductor materials, and placed on a substrate layer, said structure comprising at least one buffer layer and at least one barrier layer, said layers being stacked alternately;
        b) a conducting channel comprising a two-dimensional electron gas (2DEG) or a two-dimensional hole gas (2DHG), formed at the interface between said buffer layer and said barrier layer, and upon applying a bias to said transistor, becoming capable of providing electron or hole current, respectively, in said transistor between source and drain contacts;
        c) the source and drain contacts connected to said 2DEG or 2DHG conducting channel and to electrical metallisations for connecting said transistor to an electric circuit; and
        d) an internal or external metal gate electrode electrically connected to a wire contact with any single body point and either placed on a top layer of said heterojunction structure between said source and drain contacts or mechanically suspended over said top layer with no physical contact to said top layer beneath;
    (2) an Alternate Current (AC) electrode connected to said transistors and capable of generating radio-frequency (RF) millisecond square-sinus AC pulses being coupled into the body of the user; and
    (3) a microcontroller for switching between the two operational modes of the microelectronic sensor: the AC pulse-generating/emitting mode with said AC electrode and the sensing mode with said transistor or transistors;

said transistor is characterised in that a thickness of the top layer of said heterojunction structure in the open gate area is 5-9 nanometres (nm) and the surface of said top layer has a roughness of 0.2 nm or less, wherein the combination of said thickness and said roughness of the top layer creates a quantum electronic effect of operating said 2DEG or 2DHG channel simultaneously in both normally-on and normally-off operation modes of the channel, thereby making said transistor to conduct electric current through said channel in a quantum well between normally-on and normally-off operation modes of the transistor.

2. The biometric authentication device of claim 1, wherein said biometric authentication device is suitable for being integrated within a smartwatch, smartphone or in any other available personal gadget or wearable device, with or without any direct skin-contact to the microelectronic sensor.

3. The biometric authentication device of claim 2, wherein said wearable device is a bracelet, a necklace, a headband, a ring or an earring.

4. The biometric authentication device of claim 1, wherein said biometric authentication device is suitable for being integrated within a smartphone lock or car lock, within a biometric authentication module of any security system, personal computer or laptop, automated teller machine, automatic gate opener, swing gate opener, flap barrier or turnstile gate, or within a biometric authentication chip of a credit card or any identification card or tag.

5. The biometric authentication device of claim 1, wherein said biometric authentication device is suitable for use in bio-vital hemodynamic monitoring of a driver for the purpose of determining the sleepiness, tiredness, nervousness, cardio risk, stress and other conditions dangerous for driving a car.

6. A method for biometric authentication of a user comprising:
    providing a microelectronic sensor comprising:
    (1) an open-gate pseudo-conductive high-electron mobility transistor or an array thereof capable of sensing electrical signals produced by a body of the user, wherein said transistor comprises:
        a) a multilayer hetero-junction structure made of gallium nitride (GaN) and aluminium gallium nitride (AlGaN) single-crystalline or polycrystalline semiconductor materials, and placed on a substrate layer, said structure comprising at least one buffer layer and at least one barrier layer, said layers being stacked alternately;
        b) a conducting channel comprising a two-dimensional electron gas (2DEG) or a two-dimensional hole gas (2DHG), formed at the interface between said buffer layer and said barrier layer, and upon applying a bias to said transistor, becoming capable of providing electron or hole current, respectively, in said transistor between source and drain contacts;
        c) the source and drain contacts connected to said 2DEG or 2DHG conducting channel and to electrical metallisations for connecting said transistor to an electric circuit; and
        d) an internal or external metal gate electrode electrically connected to a wire contact with any single body point and either placed on a top layer of said heterojunction structure between said source and drain contacts or mechanically suspended over said top layer with no physical contact to said top layer beneath;
(2) an Alternate Current (AC) electrode connected to said transistors and capable of generating radio-frequency (RF) millisecond square-sinus AC pulses being coupled into the body of the user; and
(3) a microcontroller for switching between the two operational modes of the microelectronic sensor: the AC pulse-generating/emitting mode with said AC electrode and the sensing mode with said transistor or transistors;
said transistor is characterised in that a thickness of the top layer of said heterojunction structure in the open gate area is 5-9 nanometres (nm) and the surface of said top layer has a roughness of 0.2 nm or less, wherein the combination of said thickness and said roughness of the top layer creates a quantum electronic effect of operating said 2DEG or 2DHG channel simultaneously in both normally-on and normally-off operation modes of the channel, thereby making said transistor to conduct electric current through said channel in a quantum well between normally-on and normally-off operation modes of the transistor;
contacting a single sensing point on the body of the user with said microelectronic sensor, or activating said microelectronic sensor on calling or when contact is established;
switching said microelectronic sensor to the AC pulse-generating mode for emitting the RF signals in a form of millisecond AC pulses with the metal electrode and coupling said pulses in the body of the user;
switching said microelectronic sensor to the transistor sensing mode for recording electrical signals combined with the reflected RF signals received from the body of the user in a form of a source-drain electric current of the transistor over time (defined as IDs dynamics) with said microelectronic sensor;
transmitting the recorded signals from said microelectronic sensor to a user interface, server, remote storage, internet storage or biometric authentication cloud for further processing; and
processing the transmitted signals, correlating and comparing said IDs dynamics with pre-calibrated and stored biometric data of the user, thereby biometrically authenticating the user.

7. The method of claim 6, wherein the emitted AC pulses are in the range of 100 MHz to 100 GHz frequency domain on a signal line through the body of the user.

8. The method of claim 6, wherein the grounds of the metal electrode and of the transistors are connected.

9. The method of claim 6, wherein said multilayer heterojunction structure comprises:
A. (i) one top AlGaN layer recessed in an open gate area of the transistor to the thickness of 5-9 nm and having the surface roughness of 0.2 nm or less, and (ii) one bottom GaN buffer layer; said layers have Ga-face polarity, thus forming the two-dimensional electron gas (2DEG) conducting channel in said GaN layer, close to the interface with said AlGaN layer; or
B. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have Ga-face polarity, thus forming a two-dimensional hole gas (2DHG) conducting channel in the top GaN layer, close to the interface with said AlGaN barrier layer; or
C. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer; or
D. (i) one top AlGaN layer recessed in an open gate area of the transistor to the thickness of 5-9 nm and having the surface roughness of 0.2 nm or less, and (ii) one bottom GaN buffer layer; said layers have N-face polarity, thus forming a two-dimensional hole gas (2DHG) conducting channel in the GaN buffer layer, close to the interface with said AlGaN barrier layer.

10. The method of claim 6, wherein the source and drain contacts of the transistor are ohmic.

11. The method of claim 6, wherein the electrical metallisations of the transistor are capacitively-coupled to the 2DEG or 2DHG conducting channel for inducing displacement currents, thus resulting in said source and drain contacts being non-ohmic.

12. The method of claim 6, wherein the transistor further comprises a dielectric layer deposited on top of the multilayer heterojunction structure of the transistor and under the metal electrode.

13. The method of claim 6, wherein said substrate is GaN having a thickness of 0.5-2 µm.

14. The method of claim 6, wherein the thickness of the top layer of the transistor in the open gate area is 6-7 nm.

15. The method of claim 14, wherein the thickness of said top layer in said open gate area is 6.2 nm to 6.4 nm.

16. The method of claim 6, wherein the metal gate electrode is connected to the source contact for discharging and allowing a fine tuning of the microelectronic sensor gain by changing voltage ($V_{DS}$).

17. The method of claim 16, wherein the connection of said metal gate electrode to said source contact is high-ohmic and established via a capacitor for preventing the strong signal decay.

18. The method of claim 6, wherein the metal gate electrode is external and common for each of the transistors in said microelectronic sensor and either placed on said transistors or mechanically suspended over said transistors at a height of 10-100 nm, without physical contact with said transistors.

19. The method of claim 6, wherein said user interface is a smartphone, smartwatch, mobile device, personal electronic gadget, or desktop computer.

20. The method of claim 6, wherein said microelectronic sensor further comprises:
a voltage source connected to the electrical contact lines of the transistors via an electric circuit for supplying electric current to said transistors;
an integrated or complementary metal-oxide-semiconductor (CMOS) current amplifier connected to said voltage source for amplification of an electric current obtained from said transistors;
an analogue-to-digital converter (ADC) with in-built digital input/output card connected to said current amplifier for outputting a converted signal to a user interface with or without any direct skin-contact; and
a connection module for connecting the microelectronic sensor to the user interface.

21. The method of claim 20, wherein the connection module is a wireless communication module, selected from:
- a short-range Bluetooth or near-field communication (NFC) providing wireless connection between the wearable device and a smartphone, smartwatch or to any other available personal gadget for up to 20 m, Wi-Fi providing the wireless connection in the range up to 200 m, or
- Global system for mobile communications (GSM) providing worldwide communication to the biometric authentication cloud.

22. The method of claim 20, wherein the converted signal is outputted to the user interface either with or without any direct skin-contact.

23. The method of claim 6, wherein said microelectronic sensor is connected to a frame or chassis or to capacitive sensitive display elements of a smartphone, smartwatch or personal electronic gadget, and said smartphone, smartwatch or personal electronic gadget are capable of transducing an electrical charge to said microelectronic sensor.

24. The method of claim 6, wherein said microelectronic sensor is a fingerprint sensor within a smartphone lock or a car lock, or the microelectronic sensor for bio-vital hemodynamic monitoring of a car driver for the purpose of determining the sleepiness, tiredness, nervousness, cardio risk, stress, or other conditions dangerous for driving a car.

* * * * *